US008278485B2

(12) United States Patent
Barbanti et al.

(10) Patent No.: US 8,278,485 B2
(45) Date of Patent: *Oct. 2, 2012

(54) PROCESS FOR THE PRODUCTION OF 2-[4-(3- AND 2-FLUOROBENZYLOXY) BENZYLAMINO] PROPANAMIDES

(75) Inventors: Elena Barbanti, Cologno Monzese (IT); Carla Caccia, Gallarate (IT); Patricia Salvati, Arese (IT); Francesco Velardi, Cameri (IT); Tiziano Ruffilli, Vigliano Biellese (IT); Luigi Bogogna, Vaprio d'Agogna (IT)

(73) Assignee: Newron Pharmaceuticals S.p.A., Bresso (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/288,891

(22) Filed: Nov. 3, 2011

(65) Prior Publication Data

US 2012/0157712 A1 Jun. 21, 2012

Related U.S. Application Data

(63) Continuation of application No. 12/338,825, filed on Dec. 18, 2008, now Pat. No. 8,076,515, which is a continuation-in-part of application No. PCT/EP2007/005105, filed on Jun. 8, 2007.

(30) Foreign Application Priority Data

Jun. 19, 2006 (EP) .................................... 06012565

(51) Int. Cl.
*C07C 231/12* (2006.01)
*C07C 233/09* (2006.01)
*A61K 31/165* (2006.01)

(52) U.S. Cl. .................... 564/165; 564/167; 514/620

(58) Field of Classification Search .................. None
See application file for complete search history.

(56) References Cited

U.S. PATENT DOCUMENTS

| 5,391,577 | A | 2/1995 | Dostert et al. |
| 6,306,903 | B1 | 10/2001 | Pevarello et al. |
| 8,076,515 | B2 * | 12/2011 | Barbanti et al. ............. 564/165 |
| 2004/0248978 | A1 | 12/2004 | Salvati |
| 2006/0079570 | A1 | 4/2006 | Salvati et al. |
| 2007/0093495 | A1 | 4/2007 | Ruggero et al. |
| 2007/0203182 | A1 | 8/2007 | Besana et al. |
| 2007/0276046 | A1 | 11/2007 | Salvati et al. |
| 2008/0096965 | A1 | 4/2008 | Barbanti et al. |
| 2008/0132567 | A1 | 6/2008 | Barbanti et al. |
| 2010/0016437 | A1 | 1/2010 | Salvati et al. |
| 2010/0324141 | A1 | 12/2010 | Barbanti et al. |
| 2011/0014304 | A1 | 1/2011 | Izzo et al. |

FOREIGN PATENT DOCUMENTS

| EP | 0 400 495 A1 | 12/1990 |
| EP | 1 655 029 A | 5/2006 |
| WO | WO 2004/066987 A2 | 8/2004 |
| WO | WO 2005/040138 A1 | 5/2005 |
| WO | WO 2005/102300 A1 | 11/2005 |
| WO | WO 2006/027052 A2 | 3/2006 |

OTHER PUBLICATIONS

Cattabeni, 2004, "Ralfinamide," *Idrugs, Current Drugs Ltd*. 935-939.
Mealy et al., 2002, "Neurologic Drugs," *Drugs of the Future* 27(9):879-915.
PCT International Search Report from PCT/EP2007/005105 dated Aug. 23, 2007.
Pevarello et al., 1998, "Synthesis and anticonvulsant activity of a new class of 2-[(arylaklyl)amino]alkanamide derivatives," *J. Med. Chem.* 41:579-590.
Pevarello et al., 1996, "Reductive alkylation of alpha-aminoamides," *Org. Prep. Proc. Int.* 28:179-183.
Stummann et al., 2005, "The anti-nociceptive agent ralfinamide inhibits tetrodotoxin-resistant and tetrodotoxin-sensitive Na+ currents in dorsal root ganglion neurons," *European Journal of Pharmacology* 510:197-208.

* cited by examiner

*Primary Examiner* — Brian J Davis
(74) *Attorney, Agent, or Firm* — Dechert LLP

(57) ABSTRACT

A process for obtaining therapeutically active 2-[4-(3- and 2-(fluorobenzyloxy)benzylamino]propanamides and their salts with pharmaceutically acceptable acids with high purity degree, in particular, with a content of dibenzyl derivatives impurities lower than 0.03%, preferably lower than 0.01% by weight.
The process is carried out by submitting the Schiff bases intermediates 2-[4-(3- and 2-fluorobenzyloxy)benzylideneamino]propanamides to catalytic hydrogenation in the presence of a heterogeneous catalyst in a protic organic solvent.

50 Claims, 1 Drawing Sheet

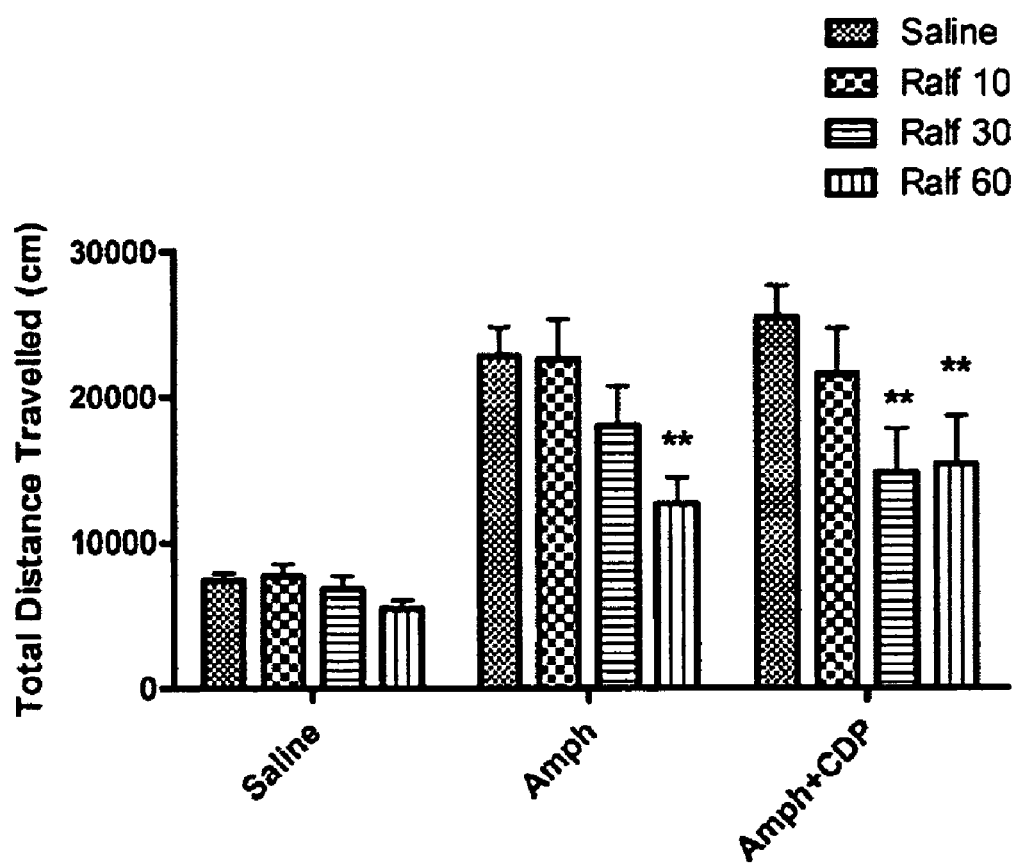

PROCESS FOR THE PRODUCTION OF 2-[4-(3- AND 2-FLUOROBENZYLOXY) BENZYLAMINO] PROPANAMIDES

CROSS REFERENCE TO RELATED APPLICATIONS

This is a continuation of U.S. patent application Ser. No. 12/338,825, filed Dec. 18, 2008 now U.S. Pat. No. 8,076,515 B2, which is a Continuation-In-Part application of International Application No. PCT/EP2007/005105, filed Jun. 8, 2007, designating the U.S., which claims the benefit of European patent application no. 06012565.5, filed Jun. 19, 2006, the disclosures of which are incorporated herein by reference in their entireties.

FIELD OF THE INVENTION

The present invention relates to a new process for the production of (S)-2-[4-(3-fluorobenzyloxy)-benzylamino] propanamide, i.e. safinamide (Ia) and (S)-2-[4-(2-fluorobenzyloxy)-benzylamino]propanamide, i.e. ralfinamide (Ib) and their salts, in high yields and very high enantiomeric and chemical purity. This method is also very useful for their production in large quantites.

BACKGROUND

Safinamide (NW-1015, FCE-26743A, PNU-151774E) is a sodium channel blocker, a calcium channel modulator, a monoamino oxidase B (MAO-B) inhibitor, a glutamate releasing inhibitor and a dopamine metabolism modulator.

Safinamide is useful in the treatment of CNS disorders, in particular of epilepsy, Parkinson's disease, Alzheimer's disease, depression, restless legs syndrome and migraine (WO 90/14334, WO 04/089353, WO 05/102300, WO 04/062655).

Ralfinamide (NW-1029, FCE-26742A, PNU-0154339E) is a sodium channel blocker useful in the treatment of pain conditions, including chronic pain and neuropathic pain, migraine, bipolar disorders, depressions, cardiovascular, inflammatory, urogenital, metabolic and gastrointestinal disorders (WO 99/35125, WO 03/020273, WO 04/062655, WO 05/018627, WO 05/070405, WO05/102300, WO 06/027052).

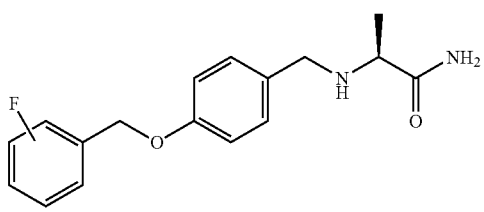

safinamide (Ia): 3-F
ralfinamide (Ib): 2-F

SUMMARY

It has now been discovered that the large scale preparations of safinamide and ralfinamide according to the methods described in the prior art, contain two undesired impurities, i.e., respectively, (S)-2-[3-(3-fluorobenzyl)-4-(3-fluorobenzyloxy)-benzylamino]propanamide (IIa) and (S)-2-[3-(2-fluorobenzyl)-4-(2-fluorobenzyloxy)-benzylamino]propanamide (IIb), and their salt, in particular the respective methanesulfonates (IIc) and (IId)

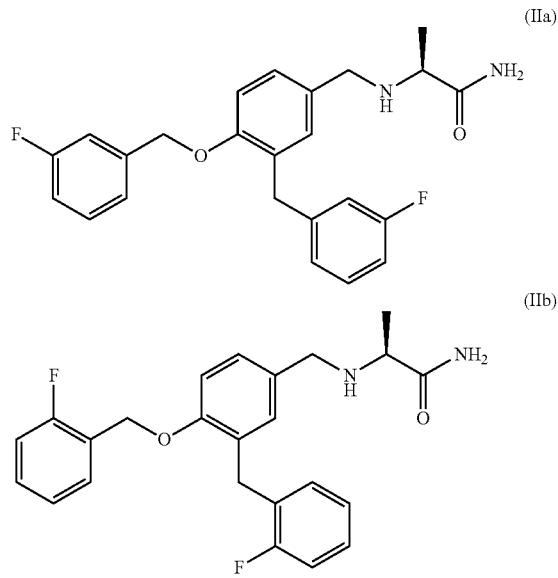

This fact is of particular relevance because of the very high toxicity of the two impurities named above.

BRIEF DESCRIPTION OF THE FIGURES

FIG. 1 provides total locomotor activity over 30 min. Mice were treated with ralfinamide (10; 30 and 60 mg/kg, po); or saline and returned to their home cage. After 30 min they received an injection of Amph (2.5 mg/kg; ip); Amph/CDP mixture (2.5 and 3.125 mg/kg; ip) or saline immediately prior to be placed in the test cage. Locomotor activity was recorded for 30 min. Two-way ANOVA shows a main effect of Amph treatment ($p<0.0001$) and of ralfinamide treatment ($p=0.0002$) but not an interaction of the two ($p=0.202$). Bonferroni's multiple comparison tests shows a statistical difference of ralfinamide 30 and 60 versus Amph/CDP mixture; and for ralfinamide 60 versus Amph alone  $P<0.01$; * $P<0.001$. n=12 mice per group.

DETAILED DESCRIPTION

Many of the drug candidates fail in clinical trials because of unforeseen effects on human metabolism, or toxicity, due to unwanted impurities and, therefore, the elimination of such impurities in early pre-clinical phase is important and strongly desirable.

At preclinical level, the "drugability" of new compounds can be assessed using a very well established battery of in vitro assays, such as interaction with drug-metabolizing enzymes, cytotoxicity, metabolic stability and profiling, membrane permeability, intrinsic clearance and human ether-a-go-go related gene (HERG) channel blockade etc.

The Cytochrome P450 (CYP 450) system is the principal enzyme system for the metabolism of lipophilic xenobiotics, including drugs, carcinogens, and environmental pollutants. CYP 450 is a heme-containing, membrane bound, multienzyme system that is present in many tissues but is present at the highest level in liver. In human liver, it is estimated that there are 15 to 20 different xenobiotic-metabolizing CYP 450 forms. So far, more than fourteen CYP gene families have been identified in mammals. Despite the existing high homology, extensive studies have revealed that each CYP family and subfamily has distinct roles in xenobiotic metabolism. Three CYP families CYP1, CYP2 and CYP3 account for about 70% of human hepatic microsomes CYPs with CYP3 accounting for approximately 30%. These CYPs are the major responsible for the metabolism of most marketed drugs.

The CYP1 family contains several members that include CYP1A1, CYP1A2 and CYP1B1 and they are involved in the metabolism of acetaminophen, clomipramine and imipramine.

The CYP2 family contains several subfamilies including CYP2A, CYP2B, CYP2C, CYP2D and CYP2E. The CYP2C subfamily contains at least seven members. CYP2C9 is responsible for the metabolism of ibuprofen, diclofenac, tolbutamide and torsemide. CYP2C19 is the major isoenzyme metabolizing diazepam and omeprazole. CYP2D6 has been shown to be responsible for metabolizing over 30% of the drugs on the market, including, antidepressants and cardiovascular and anti-psychotic drugs.

In the CYP3 family, three isoforms have been identified in human liver. Human CYP3A4 has been recognized to be the most important isoform in drug metabolism. To date, metabolism catalyzed by CYP3A4 is the major elimination route for nearly 50% of marketed drugs.

Because of their importance in drug metabolism, both CYP3A4 and CYP2D6 are often involved in drug-drug interactions and several clinically used compounds have been identified as potent inhibitor of these CYP 450 isoforms such as ketoconazole, terfenadine, erythromycin, miconazole propanolol and quinidine, respectively. This imposes a clear limitation on the use of these drugs.

A further problem, consisting in sudden death as a side effect of the action of non antiarrhytmic drugs, is a major pharmacological safety concern facing the pharmaceutical industry and the health regulatory authorities. In recent years, at least five blockbusters drugs (astemizole, sertindole, terfenadine, cisapride, grepafloxacin) have been withdrawn from the market due to reports of sudden death. In all cases, long QT Syndrome (LQTS), an abnormality of cardiac muscle repolarization, that is characterized by the prolongation of the QT interval in the electrocardiogram, was implicated as a predisposing factor for "torsades de pointes", a polymorphic ventricular tachycardia that can spontaneously degenerate to ventricular fibrillation and cause sudden death. Congenital LQTS can be traced back to several possible mutations resulting in defects in sodium channels, and two different potassium channels: the rapidly activating delayed rectifier ($I_{Kr}$) and the slowly activating delayed rectifier ($I_{Ks}$). Importantly, virtually every case of a prolonged duration of cardiac action potential related to drug exposure (acquired LQTS) can be traced to one specific mechanism: blockade of $I_{Kr}$, current in the heart. This current, a major contributor to phase 3 repolarization at the end of QT interval, is conducted by tetrameric pores, with the individual subunits encoded by HERG. With blockade of HERG $K^+$ channels widely regarded as the predominant cause of drug-induced QT prolongation, early detection of compounds with this undesirable side effect has become an important objective in the pharmaceutical industry.

Compounds with strong inhibition of drug-metabolizing enzymes, in particular CYP 450 enzymes, and HERG channel blocking properties have a high probability to be toxic and that their development has to be stopped at an early-stage.

As shown in the Table 1 the impurities (IIa and IIb), as the methanesulfonate salt (IIc and IId), strongly inhibit in the micro- and submicro-molar range CYP3A4, CYP2D6, CYP2C19, CYP2C9 and HERG currents and are highly cytotoxic, compared with safinamide methanesulfonate (Ic) and ralfinamide methanesulfonate (Id) with high purity degrees, synthetized using the process of this invention.

TABLE 1

| Compound | HERG $IC_{50}$, µM | Cytotoxicity $IC_{50}$, µM | CYP3A4 $IC_{50}$, µM | CYP2D6 $IC_{50}$, µM | CYP2C19 $IC_{50}$, µM | CYP2C9 $IC_{50}$, µM | CYP1A2 $IC_{50}$, µM |
|---|---|---|---|---|---|---|---|
| Impurity IIc | 1.20 | 6.70 | 0.05 | 0.77 | 0.42 | 7.29 | >40 |
| Safinamide methanesulfonate | 27.0 | 248.0 | >40 | >40 | 23.85 | >40 | >40 |
| Impurity Iid | 2.66 | 15.00 | 0.05 | 0.92 | 1.89 | 8.01 | >40 |
| Ralfinamide methanesulfonate | 18.0 | >300 | >40 | >40 | >40 | >40 | >40 |

Table 2 shows comparative results ($IC_{50}$) about the inhibition of the cytocrome CYP3A4 using highly pure safinamide and ralfinamide methanesulfonate, synthesized using the new process of this invention, with safinamide and ralfinamide obtained with the same process in the presence of 0.3% of the impurity IIc and IId, respectively.

When 0.3% of the impurities IIc and IId are added to highly pure safinamide and ralfinamide methanesulfonate, a significant decrease in $IC_{50}$ on CYP3A4 is observed in both cases meaning that the impurities contribute to a strong inhibition of the enzyme activity.

TABLE 2

| Compound | CYP3A4 $IC_{50}$, µM |
|---|---|
| Safinamide methanesulfonate | >40 |
| Safinamide methanesulfonate plus 0.3% IIc impurity | 18 |
| Ralfinamide methanesulfonate | >40 |
| Ralfinamide methanesulfonate plus 0.3% IId impurity | 7.76 |

As shown in Table 3 the impurity (IIc) increases, starting from 3 mg/kg ip, the mortality in the mice Maximal Electroshock (MES) test without any pharmacological activity, i.e. protection from convulsions.

TABLE 3

| Compound | MES | | | | | |
|---|---|---|---|---|---|---|
| | 3 mg/kg ip | | 10 mg/kg ip | | 30 mg/kg ip | |
| | % protection | dead/live | % protection | dead/live | % protection | dead/live |
| Safinamide methanesulfonate | 50 | 0/10 | 100 | 0/10 | 100 | 0/10 |
| Impurity IIc | 0 | 5/10 | 0 | 4/10 | 0 | 4/10 |

Table 4 reports that the impurity IId, when given p.o. at 10 and 20 mg/kg, in the Maximal Electroshock test (MES) doesn't protect mice from convulsions if compared with the same doses of ralfinamide methanesulfonate.

TABLE 4

| Compound | MES | | | |
|---|---|---|---|---|
| | 10 mg/kg p.o. | | 20 mg/kg p.o. | |
| | Protection % | Dead/live | | Dead/live |
| Ralfinamide methanesulfonate | 60% | 0/10 | 90% | 0/10 |
| Impurity IId | 0% | 0/10 | 0% | 0/10 |

Based on all these data, the impurities IIc and IId, present in safinamide and ralfinamide, respectively, synthesized with the process described in WO 90/14334 and by Pevarello et al in J. Med. Chem, 1998, 41, 579-590 show in vitro some undesirable features, such as cellular toxicity, strong inhibition of some isoform of CYP 450, HERG channel blockade and no protective activity in an "in vivo" model of epilepsy.

One of the important aspects of CYP is the variation among different population groups. Variations in drug metabolism are of great importance in clinical studies. Considerable variation in the enzymatic activity of CYP3A4 and CYP2D6 has been demonstrated between different ethnic groups and even among different individuals in the same ethnic group. The difference in the CYP activity among individuals varies significantly, depending upon different isoenzymes. Changes in the CYP expression level of different individuals can cause variations in drug metabolism. More importantly, polymorphism can also result in CYP enzyme variants with lower or higher enymatic activity that leads to variations in drug metabolism. CYP2D6 polymorphism is a well-studied topic in drug metabolism. In clinical studies, pronounced variations between individuals was first found in the metabolism of antihypertensive and antiepileptic drugs. Elimination of CYP2D6 metabolized drugs is slower in those individuals who carry defective CYP2D6 alleles. Individuals with slow metabolism are classified as poor metabolizers (PM), while catalytically competent individuals are called extensive metabolizers (EM): The incidence of the PM phenotype in population of different racial origin varies: approximately 5 to 10% of Caucasians are of the PM phenotype, but only 1% in Asian population. CYP2C19 is another important polymorphic isoform that has clinical implications.

Taken into account these observations, a compound that does not interfere with CYP450 isoforms (neither inhibition nor induction) has a very low risk for drug-drug interactions in clinical practice and can be simply and safely prescribed by physicians.

In particular, drugs that not interfere with the cytochromes of the CYP450 system are particularly indicated for the therapeutical treatment of individuals that are classified as poor metabolizers (PM) or for the therapeutical treatment of patients who are concomitantly consuming other drugs which are known to interact with said cytochromes, such as ketoconazole, terfenadine, erythromycin, miconazole, propanolol and quinidine, and/or are known to have HERG channel blocking properties.

Bipolar disorders are debilitating psychiatric illnesses characterised by episodes of depression and mania, which often alternate and increase in severity and frequency over time. Bipolar disorders are not easy to recognize because many symptoms overlap with other psychiatric disorders. Exact cause is unknown, but changes in the level of brain neurotransmitters, and psychosocial factors may be involved.

The pharmacology treatments so far available are various and with different mechanisms of action. The drugs currently used in clinical practice range from lithium to other substances such as valproate, carbamazepine and lamotrigine.

For most of these drugs the mechanisms of action at the molecular levels are not completely understood, and current knowledge indicates that most of these drugs have more than one mechanism of action, each of which may contribute to therapeutic efficacy to a variable extent depending on the condition being treated. It would seem likely that the clinical efficacy of these drugs in the treatment of psychiatric disorders is related to multifactorial mechanisms. It is known that not all anticonvulsants are active in bipolar disorders as for example gabapentin (Frye at al, J. Clinical. Pharmacol.; 2000 20: 607-614; Pande et al, Bipolar Disord.; 2000 2: 249-55), levetiracetam (Grunze et al, J. Clin. Psychiatry; 2003 64: 781-4) and tiagabine (Yatham et al, J. Clin. Psychiatry; 2004 65(suppl.10): 28-35). Therefore, the fact that compounds of the present invention show antiepileptic activity in some models (WO90/14334) does not necessarily imply activity in bipolar disorders.

According to the common clinical practice, safinamide and ralfinamide methanesulfonates (Ic and Id) are usually administered to the patient in need thereof for a long period of time, subdivided in several daily dose. This is particularly the case of therapeutical applications wherein the disease to be treated is: Parkinson's disease, Alzheimer's disease and restless legs syndrome (for the use of Safinamide) or chronic or neuropathic pain, cardiovascular or inflammatory disorders (for the use of Ralfinamide). Although the daily dosage may vary according to the specific conditions and needs of the patients, the safinamide methanesulfonate daily dosage may usually range from 10 mg/day to 800 mg/day, while ralfinamide methanesulfonates daily dosage may usually range from 10 mg/day to 1 g/day. Under these conditions, and in consideration of the data reported above, it is highly advisable to keep the level of the impurities (IIa) and (IIb) or the salts thereof, in particular the methanesulfonate salts (IIc) and (IId) in the pharmaceutical dosage forms of safinamide and ralfinamide or the salts thereof as low as possible, in any case lower than 0.03%, preferably lower than 0.01% by weight with respect to the amount of, respectively, safinamide and ralfinamide or the salts thereof, in particular the methanesulfonate salts.

Investigations and experimental studies carried out by the inventors have shown that safinamide and ralfinamide and the respective salts with pharmaceutically acceptable acids prepared according to the prior art methods contain an amount of the respective impurities (IIa) and (IIb) or the respective salts with pharmaceutically acceptable acids, such as (IIc) and (IId), that are higher than 0.03% by weight. Therefore, the above said products are less suitable than the highly pure compounds of the invention. In particular, pharmaceutical preparations containing safinamide or ralfinamide or the salt thereof with pharmaceutically acceptable acids, wherein the content of impurities (IIa), (IIb), and the respective salts with pharmaceutically acceptable acids is not lower than 0.03%, preferably than 0.01% by weight with respect to the above said active substances, are less suitable as medicaments.

In this specification and claims the values of the above indicated limits, unless as otherwise specified, are to be intended as expressing the per cent ratio by weight of the "active substances", i.e., the effective content of the biologically active impurity (IIa, IIb) with respect to the effective content of the therapeutically active substance (Ia, Ib).

The process described in this invention by strongly reducing the impurities leads to products with high chemical purity and safer biological profile. Other impurities, barely detectable, derive from the very small quantities of 2- and 4-fluorobenzyl chloride and of 3- and 4-fluorobenzyl chloride which are contained in the commercially available 3-fluorobenzyl chloride and 2-fluorobenzyl chloride respectively, used for the synthesis of 4-(3-fluorobenzyloxy)benzaldehyde (IVa) and 4-(2-fluorobenzyloxy)benzaldehyde (IVb) intermediates for the preparation of, respectively, compounds (Ia) and (Ib). According to the process described in the present invention safinamide and ralfinamide are obtained with high yields and high purity where the content of (S)-2-[3-(3-fluorobenzyl)-4-(3-fluorobenzyloxy)-benzylamino]-propanamide (IIa) and (S)-2-[3-(2-fluorobenzyl)-4-(2-fluorobenzyloxy)-benzylamino]-propanamide (IIb), and their salt, in particular with methanesulfonic acid (generically named "dibenzyl derivatives") in safinamide and ralfinamide or the salt thereof, in particular with methanesulfonic acid, is lower than or equal to 0.03%, preferably 0.01% (by weight).

The process object of the present invention starts from 4-hydroxy-benzaldehyde and comprises the three following steps:

a) O-benzylation of 4-hydroxybenzaldehyde with derivatives of the following general formula 3- or 2-F—$C_6H_4$—$CH_2$—Y, where Y is a leaving group (Cl, Br, I, $OSO_2CH_3$ etc.); this O-benzylation is carried out under conditions which are highly selective for O-alkylation and gives 4-(3-fluorobenzyloxy)benzaldehyde and 4-(2-fluorobenzyloxy)benzaldehyde of high purity;

b) reductive alkylation of L-alaninamide, base or salt, with 4-(3-fluorobenzyloxy)benzaldehyde and 4-(2-fluorobenzyloxy)benzaldehyde, where the reducing system is hydrogen gas and a heterogeneous catalyst, for obtaining, after crystallization, safinamide and ralfinamide respectively in very high enantiomeric and chemical purity;

c) preparation of safinamide and ralfinamide salts with a pharmaceutically acceptable acid by salification of safinamide and ralfinamide respectively, obtained in the preceding step. Pharmaceutically acceptable acids are, for instance, selected from nitric, hydrochloric, hydrobromic, sulphuric, perchloric, phosphoric, methanesulfonic, p-toluensulfonic, acetic, trifluoroacetic, proprionic, glycolic, lactic, oxalic, malonic, malic, maleic, tartaric, citric, benzoic, cinnamic, mandelic and salicylic acid.

A further object of this invention is to provide safinamide and ralfinamide or their salts with a pharmaceutically acceptable acid, preferably methanesulfonic acid, with a high purity degree, in particular with a content of the respective dibenzyl derivatives of the formula (IIa) or (IIb) or the salts thereof with a pharmaceutically by acceptable acid, e.g. the methanesulfonic acid, lower than 0.03%, preferably lower than 0.01% by weight (referred to the "active substances"), which is suitable for their use as medicaments.

Moreover, another object of this invention is to provide pharmaceutical formulations comprising safinamide or ralfinamide or a salt thereof with a pharmaceutically acceptable acid, preferably methanesulfonic acid, as the active agents wherein the content of the respective dibenzyl derivatives (IIa) and (IIb) or the salt thereof with a pharmaceutically acceptable acid, e.g. methanesulfonic acid, is lower than 0.03%, preferably lower than 0.01% (by weight) with respect to the above said active agents. These new pharmaceutical formulations were neither suggested nor achievable by applying the pharmaco-toxicological knowledge regarding safinamide and ralfinamide nor by using these active agents prepared according to the methods available in the state of the art.

Therefore, said pharmaceutical formulations comprising safinamide or ralfinamide or the salts thereof with a pharmaceutically acceptable acid, preferably methanesulfonic acid, having the above said high purity degree constitute a further object of this invention.

The above said pharmaceutical formulations may optionally comprise one or more additional active agents, besides safinamide or ralfinamide or the salts thereof with a pharmaceutically acceptable acid, preferably methanesulfonic acid, having the above described high purity degree.

For instance, a new pharmaceutical formulation useful for the adjunctive treatment of Parkinson's disease or restless legs syndrome may comprise one or more adjunctive Parkinson's disease active agent(s) such as those described in WO 04/089353 and WO 05/102300, preferably a dopamine agonist and/or levodopa and/or a catechol-O-methyltransferase (COMT) inhibitor, in addition to safinamide or a salt thereof with a pharmaceutically acceptable acid, preferably methanesulfonic acid, having the above said high purity degree.

As a further example, a new pharmaceutical formulation according to this invention useful for the treatment of pain conditions, including chronic pain and neuropathic pain, and migraine may contain a further active agent such as gabapentin and pregabalin or a pharmaceutically acceptable salt thereof as described in EP 1423168, in addition to ralfinamide or a salt thereof with a pharmaceutically acceptable acid, preferably methanesulfonic acid, having the above said high purity degree.

The pharmaceutical compositions containing high purity safinamide or ralfinamide according this invention can be prepared by conventional procedures known in the art, for instance by mixing the active compounds with pharmaceutically, therapeutically inert organic and/or inorganic carrier materials. The compositions of the invention can be in liquid form, e.g. in the form of a solution, suspension, emulsion; or in solid form, e.g. tablets, troches, capsules, patches.

Suitable pharmaceutically, therapeutically inert organic and/or inorganic carrier materials useful in the preparation of the composition of the present invention include, for example, water, gelatine, arabic gum, lactose, starch, cellulose, magnesium steareate, talc, vegetable oils, polyalkyleneglycols, cyclodextrins and the like. The pharmaceutical compositions of the invention can be sterilized and may contain, besides the active ingredient(s), further components well known to the skilled in the art, such as, for example, preservatives, stabilizers, wetting or emulsifying agents, e.g. paraffin oil, mannide monooleate, salts to adjust osmotic pressure, buffers and the like.

A further object of this invention is to provide a method for treating CNS disorders, in particular epilepsy, Parkinson's disease, Alzheimer's disease and restless legs syndrome, comprising administering to a patient in need thereof an effective amount of high purity safinamide or a salt thereof with a pharmaceutically acceptable acid, preferably methanesulfonic acid, having a content of dibenzyl derivative (IIa) or a salt thereof with a pharmaceutically acceptable acid, preferably methanesulfonic acid, lower than 0.03%, preferably lower than 0.01% by weight (referred to the "active substances"). Said method includes treating Parkinson's disease or restless legs syndrome by administering to a patient in need thereof an effective amount of the high purity safinamide described above, optionally in conjunction with one or more Parkinson's disease active agent(s) as described in WO 2004/089353, such as, for instance, a dopamine agonist and/or levodopa and/or a catechol-O-methyltransferase (COMT) inhibitor.

Moreover, a further object of this invention is to provide a method for treating pain conditions including chronic pain and neuropathic pain, migraine, bipolar disorders, depressions, cardiovascular, inflammatory, urogenital, metabolic and gastrointestinal disorders comprising administering to a patient in need thereof an effective amount of high purity ralfinamide or a salt thereof with a pharmaceutically acceptable acid, preferably methanesulfonic acid, having a content of dibenzyl derivative (IIb) or a salt thereof with a pharmaceutically acceptable acid, preferably methanesulfonic acid, lower than 0.03%, preferably lower than 0.01% by weight (referred to the "active substances").

The above said method includes treatment of pain conditions, including chronic pain and neuropathic pain, and migraine with high purity degree ralfinamide or a salt thereof with a pharmaceutically acceptable acid, preferably methanesulfonic acid, optionally in conjunction with gabapentin or pregabalin.

In WO 90/14334, and in the paper by Pevarello et al. in J. Med. Chem., 1998, 41, 579-590, a three steps process for the preparation of benzyloxy-benzylamino-alkanamides is described:
a) synthesis of the intermediate 4-benzyloxybenzaldehydes by O-benzylation of the corresponding 4-hydroxybenzaldehydes with the suitable benzyl chlorides
b) reductive alkylation of α-amino-amides with 4-benzyloxy-benzaldehydes using sodium cyanoborohydride as a reducing agent as schematically shown here below

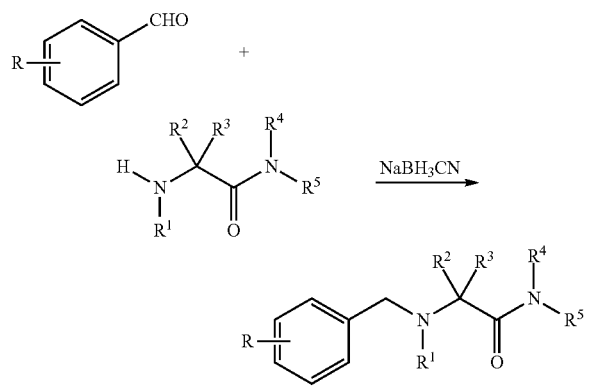

where R represents, among other substituents, 3-F and 2-F; $R^1$ represents, among other substituents, hydrogen; $R^2$ represents, among other substituents, hydrogen; $R^3$ represents, among other substituents, $CH_3$; both $R^4$ and $R^5$ represent, among other substituents, hydrogen.

In particular, as far as safinamide and rafinamide preparation is concerned, the reductive alkylation is the reductive alkylation of L-alaninamide with 4-(3-fluorobenzyloxy)benzaldehyde and 4-(2-fluorobenzyloxy)benzaldehyde respectively as shown here below

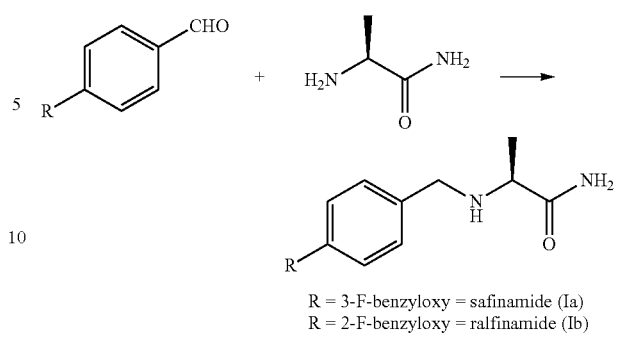

R = 3-F-benzyloxy = safinamide (Ia)
R = 2-F-benzyloxy = ralfinamide (Ib)

In J. Med. Chem. (Pevarello et al.), 1998, 41, 579-590 yields of 45% and 60% for the preparation of safinamide and ralfinamide methanesulfonate respectively, are reported, starting from the corresponding (fluorobenzyloxy)benzaldehydes.

The process described in WO 90/14334 and in the above cited paper is the same and provides a one-pot system where the iminoalkylation and the reduction are made in the same reactor. The suitable aldehyde is added all at once to a mixture of L-alaninamide hydrochloride, sodium cyanoborohydride, methanol and powdered molecular sieves.

According to Pevarello et al., in Org. Prep. Proc. Int. 1996, 28, 179-183 (where the synthesis of some α-benzylaminoamide derivatives by reductive alkylation is described), use of an α-aminoamide as hydrochloride is important for the formation of the iminium ion in place of the corresponding imine, as the iminium ion reacts more easily with sodium cyanoborohydride than with the aldehyde carbonyl group.

According to above authors, the one-pot procedure seems to avoid Schiff-base racemization problems and the molecular sieves speed up the reaction (although the yields are poor).

The cyanoborohydride is the only reducing agent utilized, and it seems that this choice is due to its low reactivity and its selectivity (see Review "Sodium Cyanoborohydride—A Highly Selective Reducing Agent for Organic Functional Groups" —C. F. Lane, Synthesis 1975, 132-146), which makes it able to distinguish between the protonated Schiff base and the starting aldehyde. The synthesis described in the paper by Pevarello et al. provides the isolation of the products by column chromatography, followed by conversion into the corresponding salts by treatment with acids. No information is provided about the enantiomeric and/or chemical purity of both safinamide and ralfinamide and/or their salts.

The method described above suffers from many drawbacks, that limit its use on large scale; herebelow some examples of said drawbacks are listed:
formation of cyanides;
formation of boron derivatives, difficult to remove from the active principles;
use of powdered molecular sieves which are physically changeable and expensive;
low yields;
low final product concentration in the reductive alkylation reaction mixture (about 2-3% weight/volume);
isolation of the products by column chromatography, which is considered a troublesome and expensive purification method when large scale preparations of active agents through chemical synthesis are involved.

Moreover, as shown in the examples which follow this description, the products obtained according to the methods described above contain an amount of impurities (IIa), (IIb), (IIc) or (IId) which is higher than 0.03% by weight with respect to the respective active substance (Ia), (Ib), (Ic) or (Id). In addition, it has been shown that it is difficult to eliminate said impurities from the final product safinamide and ralfinamide or their salts, by using commonly known purification methods such as crystallization from solvents or chromatography, which in any case imply a reduction of yields.

Synthesis of the 4-(fluorobenzyloxy)-benzaldehyde intermediates

According to the known methods, the fluorobenzyloxy-benzaldehydes intermediates for the synthesis of safinamide and ralfinamide are obtained by benzylation of 4-hydroxy-benzaldehyde in a basic medium, that is by benzylation of phenol salts which, being ambident nucleophiles, give two different products, i.e. the desired O-alkylated derivatives and the undesired C-alkylated derivatives.

It has been effectively found that the fluorobenzylation of 4-hydroxybenzaldehyde with 3-fluorobenzyl chloride, performed according to the known methods, gives the 4-(3-fluorobenzyloxy)benzaldehyde (IVa) as the main product together with 3-(3-fluorobenzyl)-4-(3-fluorobenzyloxy)benzaldehyde (Va) that derives from the alkylation of both the hydroxy group in position 4 and carbon atom in position 3 of the 4-hydroxybenzaldehyde. The same happens in the fluorobenzylation of 4-hydroxybenzaldehyde with 2-fluorobenzyl chloride according to the following scheme:

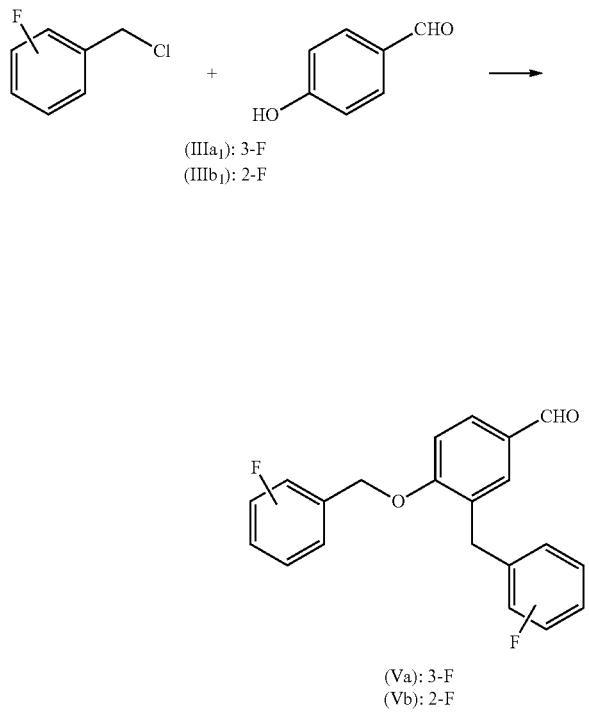

The reductive alkylation of L-alaninamide with an aldehyde which contains the di-alkylated impurity gives a safinamide or ralfinamide end product which is also impure of the respective di-alkylated compound, the di-benzyl derivative, whether as a free base (IIa) or (IIb) or a salified compounds, preferably with methanesulfonic acid (IIc) or (IId), as shown in the following scheme:

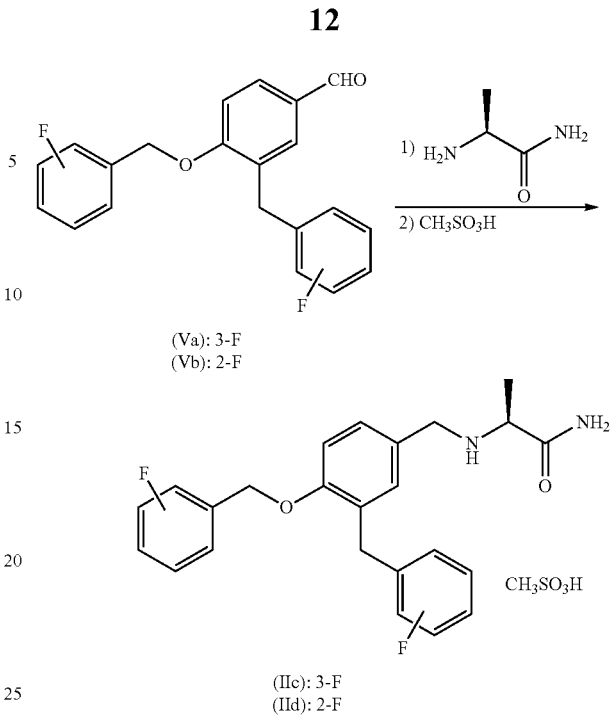

Other pharmaceutically acceptable acids, e.g. nitric, hydrochloric, hydrobromic, sulphuric, perchloric, phosphoric, methanesulfonic, p-toluensulfonic, acetic, trifluoroacetic, proprionic, glycolic, lactic, oxalic, malonic, malic, maleic, tartaric, citric, benzoic, cinnamic, mandelic and salicylic acid can be used in the place of the preferred methanesulfonic acid. The mono-alkylated derivative (safinamide or ralfinamide) and the corresponding di-alkylated impurities have similar chemical-physical properties and this makes difficult the purification of safinamide and ralfinamide with traditional methods.

Furthermore the known methods suffer from these additional drawbacks:
1) the use of a lower alcohol as a solvent; in basic conditions, the solvent, for example methanol, can act itself as a nucleophilic reagent and gives, with 3- or 2-fluorobenzyl chloride, a certain amount of methyl-fluorobenzyl-ether;
2) the extraction of the final product with a water-immiscible organic solvent is possible only after the alcoholic reaction solvent has been eliminated from the reaction mixture.

It has now been found that by using the above methods, in order to obtain a final product of formula (Ia) or (Ib) wherein the content of the respective impurity (Ia) or (IIb) is lower than 0.03% (by weight), it is necessary to drastically purify the intermediate 4-(3-fluorobenzyloxy)benzaldehyde (IVa) or 4-(2-fluorobenzyloxy)benzaldehyde (IVb) to reduce content of the respective impurities of formula (Va) and (Vb).

Said purification is preferably carried out by submitting the reaction products to crystallization, more preferably by adding to a solution of the crude compound (IVa) or (IVb) in an inert organic solvent a miscible inert organic non-solvent. The organic inert solvent is preferably selected from the aromatic hydrocarbons and, more preferably, is toluene. The miscible inert organic non-solvent is preferably selected from the lower aliphatic hydrocarbons, more preferably is n-hexane. A further crystallization procedure may consist in dissolving the above said compounds (IVa) or (IVb) into a hot solvent, e.g. cyclohexane or a di($C_3$-$C_4$)alkyl ether, such as diisopropyl ether at reflux, and then cooling the solution at room temperature, preferably at 10-15° C., most preferably, with inducing crystallization by addition of pure crystals of the pure compound (IVa) or (IVb).

According to one aspect of this invention, it has now surprisingly been found that when the reaction between an alkylating agent of formula (IIIa) or (IIIb) (see the scheme below where the F atom is in position 2 or 3 and Y is a leaving group such as, for example, Cl, Br, I, $OSO_2CH_3$, $OSO_2C_6H_4$-$pCH_3$, etc.) and 4-hydroxybenzaldehyde, is carried out under phase-transfer conditions, the corresponding 4-(fluorobenzyloxy)benzaldehydes are obtained in high yields and with very low level of C,O-bis-alkylated impurities.

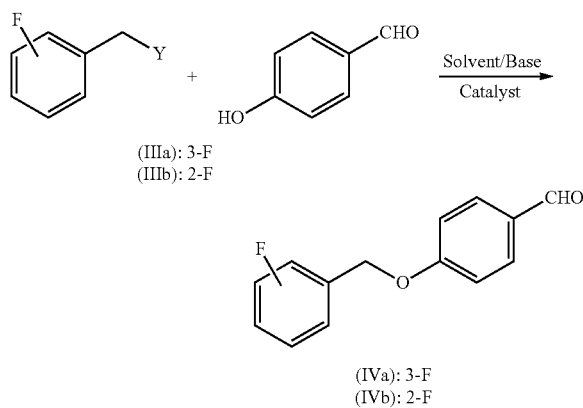

(IIIa): 3-F
(IIIb): 2-F (IVa): 3-F
(IVb): 2-F

This new fluorobenzylation of 4-hydroxybenzaldehyde under phase-transfer conditions can be made both in a solid/liquid system, where in the liquid organic phase the reagents and the phase-transfer catalyst are dissolved and the solid phase is constituted by the inorganic base or the 4-hydroxybenzaldehyde salt (possibly generated in situ from 4-hydroxy-benzaldehyde and the inorganic base itself), and in a liquid/liquid organic/aqueous system where the inorganic base is dissolved in the aqueous phase.

A preferred system is the solid/liquid system wherein the inorganic base is preferably selected from $Na_2CO_3$, $K_2CO_3$, KOH, NaOH.

The organic solvents used in the reaction, both in the case of the liquid/liquid system and of the solid/liquid system, can be dialkyl ethers such as, for example, di-tert-butyl ether, ethyl-tert-butyl ether, or aromatic hydrocarbons such as, for example, toluene, ethylbenzene, isopropylbenzene and xylenes. All these solvents can be easily recovered by distillation.

The phase-transfer catalysts employed can be quaternary ammonium or phosphonium salts such as, for example, tetrabutyl ammonium bromide, tetradecyltrimethyl ammonium bromide, hexadecyltributyl phosphonium bromide, tricaprilylmethyl ammonium chloride (Aliquat), methyltrialkyl ($C_8$-$C_{10}$)ammonium chloride (Adogen), the tetradecyltrimethyl ammonium bromide being the preferred one.

Also polyethyleneglycols of low molecular weight can be used as phase-transfer catalysts such as, for example, PEG-200 (CAS 25322-68-3) or PEG-400 (CAS 25322-68-3).

The quantity of phase-transfer catalyst used is between 0.02-1 mol per mole of 4-hydroxybenzaldehyde, preferably between 0.1-1 mol per mole of 4-hydroxybenzaldehyde as, in these conditions, the quantity of the C,O-bis-fluorobenzylated impurities may result to be less than 0.03%, preferably equal to 0.01% or less by weight.

The ratio between the alkylating agents of formula (IIIa) or (IIIb) and 4-hydroxybenzaldehyde is between 0.6 and 1.5, preferably between 0.9 and 1.1.

The reaction temperature is between 60° C. and 160° C., the preferred interval being between 80° C. and 120° C.

The reaction time is generally between 4 and 8 hours.

The reaction yields are very high, as a rule more than 90%.

The reaction productivity, i.e. the concentration of the reaction products in the reaction mixture is very high in the reaction condition described, normally is more or equal to 25% (weight/volume).

Synthesis of Safinamide and Ralfinamide by Reductive Alkylation of α-Aminoamides The state of the art would suggest to the expert in the field that the reductive alkylation of α-amino-amides with 4-(3- or 2-fluorobenzyloxy)benzaldehydes using hydrogen and a heterogeneous catalyst as a reducing agent, should not be suitable for the preparation of safinamide and ralfinamide because of the incompatibility among the reagents and the final products and the reduction conditions.

In fact, it is well known how easily benzaldehydes are reduced to benzyl alcohols or even to the corresponding hydrocarbons, as well as it is known that the conditions which should be used to perform a reductive alkylation with hydrogen and a heterogeneous catalyst, are normally the same conditions used to break the bonds between a benzylic carbon atom and heteroatoms like nitrogen or oxygen, the kind of bonds that are present both in safinamide and ralfinamide and in their precursors.

In fact, the benzylic group is normally employed as a protecting group of phenols or amines (see "*Protective Groups in Organic Synthesis*", T. W. Greene and P. G. M. Wuts, $3^{rd}$ Edition, 1999, John Wiley & Sons, Inc.) because of the easiness of its introduction and successive removal by catalytic reduction. In the reductive alkylation for obtaining safinamide and ralfinamide, one could expect the formation of many by-products, some of which are reported here below:

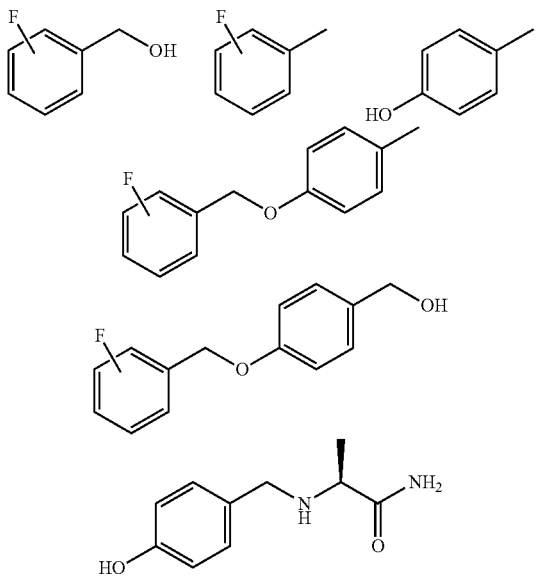

The fact that safinamide and ralfinamide have been obtained in very high yields and purity by reductive alkylation of L-alaninamide, with 4-(3- or 2-fluorobenzyloxy)benzaldehyde, using hydrogen and a heterogeneous catalyst as a reducing system, is a surprising and innovative aspect of this synthetic procedure.

Moreover, the reaction conditions which are used according to this procedure are easily applicable to the production in bulk.

The reductive alkylation, object of the present invention, is performed in two steps:
a) formation of the Schiff base
b) catalytic reduction of the Schiff base The two steps can be performed in succession in the same reactor (one pot reaction) either with, or without, isolation of the Schiff base, in both cases with high yields.

In the case of isolation of the Schiff base, the experimental conditions applied for its formation allow to obtain the isolated Schiff base in the form of a precipitate in high yields and very pure form.

The Schiff base preparation is suitably performed in an organic protic solvent, that must be inert vs. the reagents and the products and also inert vs. the reduction conditions of the iminic double bond, such as for example, a ($C_1$-$C_5$) lower alkanol, preferably methanol, ethanol and isopropanol.

The formation of Schiff base must be complete and this is a relevant factor for having high yields in the subsequent catalytic reduction step. It is therefore preferable to isolate the Schiff bases (VIa) and (VIb) before performing the reduction of the iminic double bond.

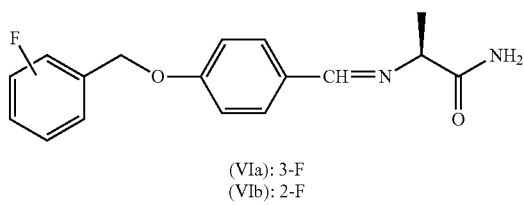

(VIa): 3-F
(VIb): 2-F

The isolated imino compounds (VIa) and (VIb) are useful intermediates for the preparation of safinamide and ralfinamide, respectively, according to this invention.

Alternatively one can favour the iminoalkylation reaction completion, by operating under such conditions as to cause the precipitation of the imino compounds (VIa) and (VIb) and to submit to the catalytic reduction the suspension containing the intermediate imino derivative.

The ratio between L-alaninamide (base or salt) and 4-(3- or 2-fluorobenzyloxy)benzaldehyde can be 1:1 but also a 10% excess of L-alaninamide can be advantageously used.

The L-alaninamide may be introduced either as a free base or as an acid addition salt thereof. Preferably, it is introduced in the reaction mixture as a salt, most preferably as hydrochloride salt, together with the stoichiometric amount of a base, preferably a tertiary amine such as, for example triethylamine or diisopropylethylamine.

The reaction temperature in the preparation of the Schiff base is comprised between 0° C. and 60° C., preferably between 20° C. and 30° C.

The reaction times are between 1 hour and 15 hours, preferably between 4 hours and 6 hours.

The reduction of the Schiff base with hydrogen and a heterogeneous catalyst is started only when the Schiff's base formation is completed: if it is started before, secondary reactions become important, sometimes prevalent, with loss in yields and purity. One of these secondary reactions, the more important, causes the formation of benzylic alcohols by reduction of the carbonyl group of the (fluorobenzyloxy) benzaldehyde of choice.

The preferred heterogeneous catalysts are nickel, rhodium, palladium or platinum catalysts, on an inert support such as, for example, carbon, alumina and silica, preferably carbon and alumina, and are used in a quantity comprised between 2% and 20% of the 4-(3- or 2-fluorobenzyloxy)benzaldehyde, preferably between 5% and 10%.

Platinum and palladium catalysts are the most preferred.

Platinum on active carbon, in particular, gives excellent results both in terms of yields, which are nearly quantitative, and selectivity, as only the iminic double bond is reduced while the bond between the benzylic carbon atom and the heteroatoms remain unchanged. It was found that safinamide and ralfinamide are surprisingly stable in the reduction reaction conditions and this is an important element in industrial production of large quantities of safinamide or ralfinamide, as an incidental reaction time prolongation wouldn't damage the final products.

The best results were obtained with wet 5% Pt/C (50% $H_2O$) and in particular with 5% Pt on carbon powder by Engelhard S.r.l., Rome, Italy.

The hydrogenation reaction is normally performed under a hydrogen pressure comprised between 1 bar and 10 bars, preferably between 3 bars and 6 bars and at temperature comprised between 10° C. and 70° C., preferably between 25° C. and 40° C.

The reduction times can vary from 1 hour to 20 hours, according to temperature, pressure, concentration, turbulence, etc., all factors well known to those skilled in the art.

The best results were obtained with reaction times of 4-6 hours.

At the end of the reaction the catalyst is recovered by filtration and reutilized or regenerated: the reaction solvent is distilled under reduced pressure, the residue is dissolved in water-immiscible organic solvent and the inorganic salts are removed by washing with water.

The final raw safinamide or ralfinamide are recovered by removing by distillation the organic solvent wherein they are dissolved.

The raw safinamide or ralfinamide are then purified by crystallization. The crystallization is preferably carried out by adding to a solution of the respective crude compound of formula (Ia) or (Ib) in an inert organic solvent a miscible inert organic non-solvent. The organic inert solvent is preferably selected from aromatic hydrocarbons such as benzene, toluene, dimethyl benzene and ethylbenzene and lower alkyl acetates and, more preferably, is ethyl acetate. The miscible inert organic non-solvent is preferably selected from the lower aliphatic hydrocarbons, such as hexane and heptane, and cyclohexane, more preferably is n-hexane The bases, are then transformed into the desired salts according to known methods, in particular they are transformed into methanesulfonate salt, which has the physical/chemical properties (stability, granulometry, flowability etc.) suitable for the subsequent formulation into a pharmaceutical preparation for use as medicament.

Example 1

Preparation of purified
4-(2-fluorobenzyloxy)benzaldehyde (IVb) by phase
transfer catalysis A mixture of 2-fluorobenzyl chloride (5 kg, 34.58 mol), 4-hydroxy-benzaldehyde (3.9 kg, 31.94 mol), potassium carbonate (4.3 kg, 31.11 mol) and tetradecyl trimethylammonium bromide (0.41 kg, 1.22 mol) in toluene (9.5 kg) is slowly brought, under stirring and under nitrogen, to reflux temperature and refluxed for 6 h.

The solution is then concentrated at room pressure, 3 kg of toluene are added and distilled off and this procedure is repeated once again.

The heterogeneous mixture is then cooled to room temperature and the solid is eliminated by filtration. The residual solvent is then eliminated under reduced pressure and to the oily residue 1.2 kg of toluene are added. The mixture is heated to about 40° C. and seeded with a few grams of pure 4-(2-fluorobenzyloxy)benzaldehyde.

The heterogeneous mixture is stirred for 15 minutes at 35-40° C. and then additioned of n-hexane (9 kg) at this temperature, in 30 minutes. After cooling to 0-5° C. and stirring for a further hour at this temperature the solid is collected by filtration and dried under reduced pressure to give 6.5 kg (87.6% yield) of 4-(2-fluorobenzyloxy)benzaldehyde; m.p. 56.7° C. (DSC, 5° C./min).

The above reaction is repeated on a 1:100 scale by using 39 g (0.319 mol) of 4-hydroxybenzaldehyde as the starting material and following the above described procedure, with the exception that, after elimination of the reaction solvent and addition of toluene to the oily residue, the obtained mixture is heated to about 30-35 (instead of 40° C.) and, after seeding with a small amount of pure 4-(2-fluorobenzyloxy)benzaldehyde, the heterogeneous mixture is stirred for 15 minutes at 30° C. (instead of 35-40° C.) before adding n-hexane. The yield is 66.8 g (90%) of 4-(2-fluorobenzyloxy)benzaldehyde, m.p. 56.7° C. (DSC, 5° C./min), having a GC purity of 92.2 (area %, see Example 16A) and a 3-(2-fluorobenzyl)-4-(2-fluorobenzyloxy)benzaldehyde content 0.01% by weight determined by GC (see Example 16B)

(*) The yields reported in this and in the following Examples, when no otherwise specified, are intended as molar yields.

1.1 Further purification of 4-(2-fluorobenzyloxy)benzaldehyde by crystallization One kilogram of the product prepared according to the procedure described in Example 1 is dissolved in 2 kg of diisopropryl ether at reflux under stirring.

The solution is cooled to 50-55° C. in 10-15 minutes and seeded with a few grams of pure 4-(2-fluorobenzyloxy)benzaldehyde.

The suspension is cooled to 10-15° C. during 45-60 minutes and stirred for an additional hour.

The precipitate is finally collected by filtration, washed with cool diisopropyl ether (0.2 Kg) and dried under reduced pressure to give 0.93 kg of 4-(2-fluorobenzyloxy)benzaldehyde with GC purity of 99.8 (area %, see Example 16A) and a content of 3-(2-fluorobenzyl)-4-(2-fluorobenzyloxy)benzaldehyde (Vb) of 0.005% by weight determined by GC according to Example 16B.

1.2 Preparation of 4-(2-fluorobenzyloxy)benzaldehyde (IVb) by phase transfer catalysis (PTC) using different catalysts 4-(2-Fluorobenzyloxy)benzaldehyde is prepared by alkylation of 4-hydroxybenzaldehyde (0.39 g) with 2-fluorobenzyl chloride by following the same procedure of Example 1, but using three different phase transfer catalysts.

The results are reported in the following Table 4

TABLE 4

| Experiment | Phase Transfer Catalyst PCT | % Vb ** | % Yield |
|---|---|---|---|
| 1.2 (a) | Tetrabutyl fosphonium bromide | 0.03 | 85.0 |
| 1.2 (b) | Aliquat 336* | 0.03 | 88.8 |
| 1.2 (c) | PEG 400 | 0.14 | 96.0 |

*Aliquat 336: tricaprylylmethylammonium chloride
** % Vb: content of 3-(2-fluorobenzyl)-4-(2-fluorobenzyloxy)benzaldehyde (% by weight)
The content of Vb is determined by GC according to Example 16B.

1.3 Preparation of 4-(2-fluorobenzyloxy)benzaldehyde (IVb) by phase transfer catalysis (PTC) in xylene 4-(2-Fluorobenzyloxy)benzaldehyde is prepared in 86.6% yield with a content of 3-(2-fluorobenzyl)-4-(2-fluorobenzyloxy)benzaldehyde of 0.02% by weight determined by GC (see Example 16B) by reacting 4-hydroxybenzaldehyde (0.39 g) with 2-fluorobenzyl chloride according to the same procedure of Example 1, but replacing toluene with xylene as the solvent.

1.4 Preparation of 4-(2-fluorobenzyloxy)benzaldehyde (IVb) by phase transfer catalysis using potassium hydroxyde as a base 4-(2-Fluorobenzyloxy)benzaldehyde is prepared in 86.7% yield with a content of 3-(2-fluorobenzyl)-4-(2-fluorobenzyloxy)benzaldehyde of 0.51% by weight determined by GC (see Example 16B) by reacting 4-hydroxybenzaldehyde (0.39 g) with 2-fluorobenzyl chloride, according to the same procedure of Example 1, but using potassium hydroxyde (0.35 mol) instead of potassium carbonate.

This product may be further purified by crystallization according to Example 1.1.

1.5 Preparation of 4-(2-fluorobenzyloxy)benzaldehyde (IVb) by phase transfer catalysis using 2-fluorobenzyl bromide 4-(2-Fluorobenzyloxy)benzaldehyde is prepared in 88.6% yield with a content of 3-(2-fluorobenzyl)-4-(2-fluorobenzyloxy)benzaldehyde of 0.07% by weight determined by GC (see Example 16B) by reacting 4-hydroxybenzaldehyde (15.6 g) with 2-fluorobenzyl bromide instead of 2-fluorobenzyl chloride according to the same procedure of Example 1.

Example 2

Preparation of (S)-2-[4-(2-fluorobenzyloxy)benzylamino]propanamide (ralfinamide, Ib) of high purity degree (one pot reaction)

An autoclave is loaded with 4-(2-fluorobenzyloxy)benzaldehyde (2.0 kg, 8.69 mol) prepared according to Example 1, and then a solution prepared apart of L-alaninamide hydrochloride (1.2 kg, 9.63 mol) and triethylamine (0.97 kg, 9.63 mol) in methanol (9.5 kg) is added thereto.

The mixture is stirred at 20-25° C. for about 1 hour and then, after seeding it with a few grams of (S)-2-[4-(2-fluorobenzyloxy)benzylideneamino]propanamide, the stirring is continued for additional 15 minutes. To the stirred heterogeneous mixture, methanol (1.6 kg) and wet (50% $H_2O$) Pt/C 5% (Engelhard cod.Escat 22, Engelhard S.r.l., Rome, Italy) (0.28 kg) are then added at 20-25° C.

The air is purged from the autoclave with nitrogen and then hydrogen is introduced at 5.0 bar and the pressure is maintained at this value during the hydrogenation course.

After 5 hours at 30-35° C. the reaction mixture is cooled to 15° C. and, after addition of methanol (4.8 kg) and heating to 40-45° C. the suspension is filtered and the solid is washed with methanol (1.6 kg).

The solvent is eliminated under reduced pressure at about 30° C. and the residue is additioned of water (5 L) at 20-25° C. on cooling and under stirring, as the water addition is an exothermic process. The heterogeneous mixture is further cooled to 15-20° C., kept at this temperature for 1 hour and then filtered. The collected solid is washed with cool water (4 L) and dried under reduced pressure to give 2.23 kg (85.0% yield) of ralfinamide with a HPLC purity of 98.8 (area %) determined according to the method of Example 17A and a C,O-dialkylated (S)-2-[3-(2-fluorobenzyl)-4-(2-fluorobenzyloxy)-benzylamino]propanamide content of 0.01% by weight determined by HPLC, according to the method of Example 17B.

2.1 Preparation of (S)-2-[4-(2-fluorobenzyloxy)benzylamino]propanamide (Ib) of high purity degree by using a palladium catalyst A mixture of 5 g of 4-(2-fluorobenzyloxy)benzaldehyde, prepared according to the Ex. 1 and the corresponding amount L-alaninamide hydrochloride and triethylamine is hydrogenated according to the same procedure of Example 2, but using wet (50% $H_2O$) Pd/C 10% instead of wet (50% $H_2O$) Pt/C 5% to obtain (S)-2-[4-(2-fluorobenzyloxy) benzylamino]propanamide (Ib) in a 70% yield.

Example 3

Preparation of (S)-2-[4-(2-fluorobenzyloxy)benzylamino]propanamide methanesulfonate (ralfinamide methanesulfonate, Id) of high purity degree Ralfinamide (2.8 kg, 9.26 mol), prepared as described in Example 2, is dissolved in iso-propanol (19.5 kg) and kept at 65-70° C. and under stirring under inert atmosphere.

After treatment with charcoal (150 g) and filtration, the solution is seeded with pure ralfinamide methanesulfonate and, methanesulfonic acid (900 g, 9.36 mol) is added in 30 minutes, under stirring and at a temperature of 50-55° C. The suspension is then cooled to 15-20° C. in 2 hours and the stirring is continued for an additional hour. The solid is finally collected by filtration and dried under reduced pressure to give 3.59 kg (97.3% yield) of ralfinamide methanesulfonate.

The HPLC purity of the obtained product is 99.8 (area %, see Example 17A) and the content of C,O-dialkylated (S)-2-[3-(2-fluorobenzyl)-4-(2-fluorobenzyloxy)-benzylamino] propanamide methanesulfonate is 0.005% by weight (see Example 17B); m.p. 240.6° C. by DSC (5° C./min).

The enantiomeric purity of ralfinamide methanesulfonate determined with a chiral HPLC column is higher than 99.8 (area %, see Example 18).

Example 4

Preparation of purified 4-(3-fluorobenzyloxy)benzaldehyde (IVa) in ethanol solution To a mixture of 4-hydroxybenzaldehyde (1.52 kg, 12.45 mol), potassium carbonate, (1.72 kg, 12.45 mol), potassium iodide (0.2 kg, 1.20 mol) in ethanol (13.0 kg), 1.8 kg, of 3-fluorobenzyl chloride (1.80 kg, 12.45 mol) are added under stirring, at room temperature.

The mixture is gradually heated to reflux and then kept at that temperature for 6 hours.

The reaction mixture is then allowed to cool to 25° C., the suspension is filtered and the solid is washed with ethanol (1.0 kg); the ethanol solutions are combined and then concentrated at reduced pressure until a residue of approximately 3.5 kg is obtained.

To this residue, toluene (5.0 kg) and water (1.7 kg) are added, the solvent mixture is stirred vigorously for 30 minutes and, after separation of the aqueous phase, the organic layer is evaporated to dryness under reduced pressure to provide crude 4-(3-fluorobenzyloxy)benzaldehyde.

To this product dissolved in 2 kg of toluene a seed of 4-(3-fluorobenzyloxy)benzaldehyde is added under stirring at 20-25° C., then n-hexane (3.8 kg) is added in 30 minutes and the mixture is cooled to 0° C. under stirring.

After 2 hours the solid is filtered and washed with n-hexane (1.3 kg). After drying, 2.6 kg (90.7% yield) of the desired product are obtained, with a gas-cromathographic purity of 99.9 (area %, see Example 16A) and a 3-(3-fluorobenzyl)-4-(3-fluorobenzyloxy)benzaldehyde content of 0.005% by weight determined by G.C. (area %, see Example 16B); m.p. 43.1° C. by DSC 5° C./min.

Example 5

Preparation of 4-(3-fluorobenzyloxy)benzaldehyde (IVa) by phase transfer catalysis A mixture of 3-fluorobenzyl chloride (5 kg, 34.58 mol), 4-hydroxy-benzaldehyde (3.9 kg, 31.94 mol), potassium carbonate (4.3 kg, 31.11 mol) and tetradecyl trimethylammonium bromide (0.41 kg, 1.22 mol) in toluene (13.5 kg) is slowly brought to reflux temperature under stirring and under nitrogen atmosphere, and then refluxed for 6 hours.

The solution is concentrated at room pressure and then 3 kg of toluene are added and distilled off. This procedure is repeated once again.

The heterogeneous mixture is then cooled to room temperature and the solid is eliminated by filtration. The residual solvent is eliminated under reduced pressure and then 1.2 kg of toluene are added to the oily residue.

The mixture is stirred at 20-25° C. and seeded with a few grams of pure 4-(3-fluorobenzyloxy) benzaldehyde, and then additioned of n-hexane (9 kg) at this temperature, in 30 minutes.

After cooling to 0-5° C. and stirring for a further hour at this temperature the solid is collected by filtration and dried under reduced pressure to give 6.5 kg (85% yield, GC purity 99.9 (area %, see Example 16A) and a 3-(3-fluorobenzyl)-4-(3-fluorobenzyloxy)benzaldehyde content of 0.008% by weight (see Example 16B).

5.1 Further purification of 4-(3-fluorobenzyloxy)benzaldehyde (IVa) by crystallization One kilogram of 4-(3-fluorobenzyloxy)benzaldehyde, prepared according to Example 5, is dissolved in 2 kg of diisopropyl ether at reflux under stirring.

The solution is cooled to 50-55° C. in 10-15 minutes and seeded with a few grams of pure 4-(3-fluorobenzyloxy)benzaldehyde.

The suspension is cooled to 10-15° C. during 45-60 minutes and stirred for an additional hour.

The precipitate is finally collected by filtration, washed with cool diisopropyl ether (0.2 kg) and dried under reduced pressure to give 0.95 kg of 4-(3-fluorobenzyloxy)benzaldehyde with GC purity of 99.9 (area %, see Example 16A) and a content of 3-(3-fluorobenzyl)-4-(3-fluorobenzyloxy)benzaldehyde lower than 0.005% by weight determined by GC (see Example 16B).

5.2 Preparation of 4-(3-fluorobenzyloxy)benzaldehyde (IVa) by phase transfer catalysis using 3-fluorobenzyl bromide 4-(3-Fluorobenzyloxy)benzaldehyde is prepared in 86.1% yield with a content of 3-(3-fluorobenzyl)-4-(3-fluorobenzyloxy)benzaldehyde of 0.07% by weight determined by GC (see Example 16B) by reacting 4-hydroxybenzaldehyde (15.6 g) with 3-fluorobenzyl bromide according to the same procedure of Example 5 but using 3-fluorobenzyl bromide instead of 3-fluorobenzyl chloride.

The so obtained 4-(3-fluorobenzyloxy)benzaldehyde is purified according to Example 5.1 to yield the title product in 97.3% yield with a content of 3-(3-fluorobenzyl)-4-(3-fluorobenzyloxy)benzaldehyde of 0.07% by weight determined by GC (see Example 16B).

5.3 Preparation of 4-(3-fluorobenzyloxy)benzaldehyde (IVa) by phase transfer catalysis using 3-fluorobenzyl methanesulfonate 4-(3-Fluorobenzyloxy)benzaldehyde is prepared in 97.5% yield with a content of 3-(3-fluorobenzyl)-4-(3-fluorobenzyloxy)benzaldehyde of 0.45% by weight, determined by GC (see Example 16B), by reacting 4-hydroxybenzaldehyde (15.6 g) with 3-fluorobenzyl methanesulfonate instead of 3-fluorobenzyl chloride according to the same procedure of Example 5. This product is further purified according to the procedure of the Example 5.1.

Example 6

Preparation of (S)-2-[4-(3-fluorobenzyloxy)benzylamino]propanamide (safinamide, Ia) of high purity degree (one pot reaction)

An autoclave is loaded with, 4-(3-fluorobenzyloxy) benzaldehyde (2.0 kg, 8.69 mol) prepared as in Example 4, and then a solution, prepared apart, of L-alaninamide hydrochloride (1.2 kg, 9.63 mol) and triethylamine (0.97 kg, 9.63 mol) in methanol (7.1 kg) is added thereto.

The mixture is stirred at 20-25° C. for 1 hour and, after seeding with few grams of (S)-2-[4-(3-fluorobenzyloxy)benzylideneamino]propanamide, stirring is continued for additional 15 minutes. To the stirred heterogeneous mixture, methanol (1.8 kg) and, wet (50% $H_2O$) Pt/C 5% (Engelhard cod. Escat 22)(0.3 kg) are then added, at 20-25° C.

The air is purged from the autoclave with nitrogen and then hydrogen is introduced at 5.0 bars.

After 5 hours at 30-35° C., the mixture is cooled to 15° C., methanol (4.8 kg) is added and the mixture is heated to 40-45° C.; finally the solid is filtered out and washed with methanol (1.6 kg).

The solvent is eliminated under reduced pressure approximately at 30° C. and then a mixture of ethyl acetate (23.0 kg) and water (18.0 kg) is added to the residue. After stirring for 15 minutes, the aqueous phase is separated and extracted with ethyl acetate (7.0 kg). The collected organic phases are concentrated until a residue of approximately 6.0 kg is obtained. To this residue n-heptane (10.8 kg) is added and the mixture is stirred at 20° C. for about 2 hours. The solid is then collected by filtration and washed with n-heptane.

After drying the solid under reduced pressure, 2.41 kg (91.8% yield) of the title compound are obtained with a HPLC purity of 98.4 (area %, see Example 17A), and a content of C,O-dibenzylated (S)-2-[3-(3-fluorobenzyl)-4-(3-fluorobenzyloxy)-benzylamino]propanamide) of 0.005% by weight (see Example 17B).

6.1 Preparation of (S)-2-[4-(3-fluorobenzyloxy)benzylamino]propanamide (Ia) of high purity degree by using a Pd catalyst (S)-2-[4-(3-Fluorobenzyloxy)benzaldehyde (5 g) in the presence of the corresponding amounts of L-alaninamide hydrochloride and triethylamine is hydrogenated according to the same procedure of Example 6, by using wet (50% $H_2O$) Pd/C 10%, instead of wet (50% $H_2O$) Pt/C 5%, to produce Ia in a 72% yield.

6.2 Preparation of (S)-2-[4-(3-fluorobenzyloxy)benzylamino]propanamide (Ia) of high purity degree by hydrogenation at 1 bar A mixture of (S)-2-[4-(3-fluorobenzyloxy)benzaldehyde, L-alaninamide hydrochloride and triethylamine is hydrogenated according to the same procedure of Example 6, but at 1 bar/$H_2$ instead of 5 bar/$H_2$.

The yield of (S)-2-[4-(3-fluorobenzyloxy)benzylamino]propanamide is 90% with a HPLC purity of 98.7 (area %, see Example 17A) and a content of (S)-2-[3-(3-fluorobenzyl)-4-(3-fluorobenzyloxy)benzylamino]propanamide of 0.005% by weight determined by HPLC (see Example 17B).

6.3 Preparation of (S)-2-[4-(3-fluorobenzyloxy)benzylamino]propanamide (Ia) of high purity degree (one pot reaction) by using L-alaninamide base (S)-2-[4-(3-fluorobenzyloxy]benzaldehyde (10 g) is reacted according to the same procedure of Example 6, but using L-alaninamide base, instead of its hydrochloride and triethylamine. The yield of (S)-2-[4-(3-fluorobenzyloxy)benzylamino]propanamide is 92% with a HPLC purity of 99.7 (area %, see Example 17A) and a content of (S)-2-[3-(3-fluorobenzyl)-4-(3-fluorobenzyloxy)benzylamino]propanamide lower than 0.005% by weight determined by HPLC (see Example 17B).

Example 7

Preparation of (S)-2-[4-(3-fluorobenzyloxy)benzylamino]propanamide methanesulfonate (safinamide methanesulfonate, Ic) of high purity degree Safinamide (2.41 kg, 7.97 mol), prepared as described in Example 6, is dissolved in ethyl acetate (56.5 kg) at 65° C. and decoloured with charcoal (100 g).

After filtration, the solution is stirred and seeded with a few grams of safinamide methanesulfonate and, after 15 minutes, methanesulfonic acid (850 g, 8.84 mol) is added in 30 minutes, at a temperature of 50-55° C. The suspension is cooled under stirring to 20-25° C. during 2 hours and stirred for an additional hour. The precipitate is finally collected by filtration and dried under reduced pressure to give 2.83 kg (89.1% yield) of safinamide methanesulfonate.

The content of impurity (S)-2-[3-(3-fluorobenzyl)-4-(3-fluorobenzyloxy)-benzylamino]propanamide methanesulfonate (IIc) measured by HPLC (see Example 17B) is of 0.005% by weight. The title compound has m.p. 216.8° C. by DSC (5° C./min).

The enantiomeric purity, measured with a chiral HPLC column, is over 99.9 (area %, see Example 19).

$^1$H-NMR ($D_2O$) (Bruker A V300) δ (ppm, with respect to $H_2O$ at 4.7 ppm): 1.43 (3H, d, J=7 Hz, $CH_3$); 2.66 (3H, s, $CH_3SO_3H$); 3.87 (1H, q, J=7 Hz, H-2); 3.97 (2H, bs, $CH_2NR$); 4.89 (2H, s, $CH_2OR$); 6.88 and 7.23 (4H, AA'XX' aromatic p-disubstituted system; 6.90÷7.22 (4H, aromatic H)

$^{13}$C-NMR ($D_2O$) (Bruker AV300) δ ppm: 15.68 ($CH_3$); 38.27 ($CH_3SO_3H$); 48.99 (CH2NR); 54.81 (CH); 69.00 ($OCH_2$); 114.15 (d, $J_{C-F}$=21 Hz, aromatic CH); 114.76 (d, $J_{C-F}$=20 Hz, aromatic CH); 115.38 (aromatic CH); 123.06 (d, $J_{C-F}$=24 Hz, aromatic CH); 123.24; 130.29 (d, $J_{C-F}$=6 Hz, aromatic CH); 131.54 (aromatic CH); 138.76 (d, $J_{C-F}$=7 Hz, aromatic CH); 158.52; 162.89 (d, $J_{C-F}$=245 Hz, C-F); 171.92 (CO)

Example 8

Preparation of (S)-2-[4-(3-fluorobenzyloxy)benzylamino]propanamide (safinamide, Ia) of high purity degree, with isolation of the intermediate Schiff base (S)-2-[4-(3-fluorobenzyloxy)benzylideneamino]propanamide (VIa)

a) (S)-2-[4-(3-Fluorobenzyloxy)benzylideneamino]propanamide (VIa)

To a suspension of 4-(3-fluorobenzyloxy)benzaldehyde (60.0 g 0.26 mol), prepared as in the Example 5 and L-alaninamide hydrochloride (35.7 g 0.29 mol) in methanol (280 mL), triethylamine (29.1 g, 0.29 mol) is added at room temperature with stirring under nitrogen atmosphere. Stirring is maintained for one additional hour.

The solution is then seeded with a few mg of (S)-2-[4-(3-fluorobenzyloxy)benzylideneamino]propanamide, the temperature is lowered to 5-10° C. and the stirring continued for 2 hours.

The solid is collected by filtration and washed with methanol at 0° C.

After drying it at reduced pressure, 57.3 g (73.2% yield) of the title compound is obtained with m.p. 112.0° C. by DSC (5° C./min).

$^1$H-NMR (DMSO-$d_6$) (Bruker AV300) δ (ppm, with respect to TMS at 2.55 ppm; DMSO solvent at 3.35 ppm): 1.31 (3H, d, J=7 Hz, $CH_3$); 3.86 (1H, q, J=7 Hz, H-2); 5.18 (2H, s, $CH_2OR$); 7.08 and 7.79 (4H, AA'XX' p-disubstituted aromatic system); 7.10-7.50 (4H, m, aromatic H); 8.27 (1H, s, CH=NR).

$^{13}$C-NMR (DMSO-$d_6$) (Bruken AV300) δ (ppm): 20.5 (CH3); 67.6 (CH); 68.4 (OCH2); 114.1 e 114.4 (d, $J_{C-F}$=21 Hz, aromatic)CH; 114.5 e 114.8 (d, $J_{C-F}$=21 Hz; aromatic CH; 114.8 (aromatic CH); 123.5 (d, $J_{C-F}$2 Hz, aromatic CH); 129.0 and 129.9 (aromatic CH); 130.4 and 130.5 (d, $J_{CF}$=7 Hz, aromatic CH); 139.6 and 139.7 (d, $J_{C-F}$=6 Hz aromatic quaternary C); 160.2; 160.5 and 163.8 (d, $J_{C-F}$=245 Hz C-F); 160.6 (CH=N); 174.8 (CO)

b) (S)-2-[4-(3-Fluorobenzyloxy)benzylamino]propanamide (Ia)

An autoclave is loaded with (S)-2-[4-(3-fluorobenzyloxy)benzylidene-amino]propanamide (16.0 g; 0.053 mol), prepared as described above, and wet (50% $H_2O$) Pt/C 5% (1.7 kg: Engelhard S.r.l., Rome, Italy) and methanol (90 mL) is added thereto. The autoclave is purged from air with nitrogen and then hydrogen is introduced at 5.0 bars. The reaction is kept at 5.0 bar and at 35° C. for 1 hour. After cooling to room temperature and elimination of the catalyst by filtration, the solvent is distilled off under reduced pressure until a residue of approximately 30 g is obtained. To this residue a mixture of ethyl acetate (150 mL) and $H_2O$ (110 mL) is added and the heterogeneous mixture is heated to 40° C., until two clear phases are obtained. These two phases are separated and the aqueous layer is extracted with 50 mL of ethyl acetate at 40° C. The organic phases are collected and evaporated to dryness. The procedure is repeated twice by adding every time 90 mL of ethyl acetate to make the product anhydrous. 95 mL of n-heptane are then added slowly and under stirring to the residue. The mixture is then maintained under stirring for 3 hours at 20° C. The solid formed is collected by filtration, washed with n-hetpane (15 mL) and dried under reduced pressure to give 15.2 g (94.8% yield) of safinamide with a HPLC purity of 99.8 (area %, see Example 17A) and a content of (S)-2-[3-(3-fluorobenzyl)-4-(3-fluorobenzyloxy)-benzylamino]propanamide lower than 0.005% by weight measured by HPLC (see Example 17B).

Example 9

Preparation of (S)-2-[4-(2-fluorobenzyloxy)benzylamino]propanamide (ralfinamide, Ib) of high purity degree, with isolation of the intermediate Schiff Base (S)-2-[4-(2-fluorobenzyloxy)benzylideneamino]propanamide (VIb)

a) (S)-2-[4-(2-Fluorobenzyloxy)benzylideneamino]propanamide (VIb)

(S)-2-[4-(2-Fluorobenzyloxy)benzylideneamino]propanamide is prepared in a 88% yield, m.p. 121° C. (capillary), by following the same procedure of Example 8, step a) but using 4-(2-fluorobenzyloxy)benzaldehyde instead of 4-(3-fluorobenzyloxy)benzaldehyde.

$^1$H-NMR: (CDCl$_3$, 300 MHz, 298K) δ (ppm, with respect to TMS): 1.46 (3H, d, J=7.0 Hz, $CH_3$); 3.91 (1H, q, J=7.0 Hz, CH—CO); 5.17 (2H, s, O—$CH_2$); 7.02 (2H, d, J=8.9 Hz aromatic H ortho to O—$CH_2$); 7.09 (1H, ddd, $J_{H-F}$=9.78 Hz $J_{orto}$=8.55 Hz $J_{meta}$=1.23 Hz aromatic H ortho to F); 7.15 (1H, dt, $J_{orto}$=7.35 Hz $J_{meta}$=1.23 Hz aromatic H para to F); 7.27-7.40 (1H, m, aromatic H para to $CH_2$); 7.48 (1H, dt, $J_{orto}$= $J_{H-F}$= 7.35 Hz $J_{meta}$=1.53 Hz aromatic H ortho to $CH_2$); 7.71 (2H, d, J=8.9 Hz aromatic H ortho to CH=N); 8.17 (1H, s, C=N)

$^{13}$C-NMR: (CDCl$_3$, 75.4 MHz, 298K) δ (ppm): 21.4 ($CH_3$); 63.8 ($OCH_2$); 68.4 ($H_2NCOCH$); 115.0 (d, $J_{C-F}$=22.4 Hz, aromatic CH), 115.5 (d, $J_{C-F}$=20.7 Hz, aromatic CH); 123.7 (d, $J_{C-F}$=14.4 Hz, quaternary aromatic C); 124.5 (bd, aromatic CH); 129.0 (quaternary aromatic C); 129.8 (bd, aromatic CH); 130.1 (bd, 2 aromatic CH); 160.5 (d, $J_{C-F}$=246.4 Hz, quaternary aromatic C); 161.1 (aromatic C-0); 161.1 (C=N); 176.9 (CONH$_2$)

b) (S)-2-[4-(2-Fluorobenzyloxy)benzylamino]propanamide (Ib)

(S)-2-[4-(2-Fluorobenzyloxy)benzylamino]propanamide is prepared in a 93% yield from (S)-2-[4-(2-fluorobenzyloxy) benzylideneamino]propanamide by following the same procedure of Example 8, step b). The content of (S)-2-[3-(2-fluorobenzyl)-4-(2-fluorobenzyloxy)-benzylamino] propanamide is 0.02% by weight determined by HPLC (see Example 17B).

Example 10

Preparation of (S)-2-[3-(3-fluorobenzyl)-4-(3-fluorobenzyloxy)-benzylamino]propanamide methanesulfonate (IIc)

a) 3-(3-Fluorobenzyl)-4-(3-fluorobenzyloxy)benzaldehyde (Va)

In a 4 L round bottomed flask kept under nitrogen atmosphere, 4-hydroxy-benzaldehyde (400 g, 3.28 mol), potassium carbonate (453 g, 3.28 mol), toluene (2 L) and 3-fluorobenzylchloride (1400 g, 9.68 mol) are added in sequence and the mixture is refluxed under stirring for 5 days. At this point a GC analysis reveals that the reaction mixture contains 4-(3-fluorobenzyloxy)benzaldehyde and 3-(3-fluorobenzyl)-4-(3-fluorobenzyloxy)benzaldehyde in a ratio of 91.4:8.6 (area/area, see Example 16A).

The reaction mixture is cooled to room temperature and then 2 L of water are added under stirring. The organic phase is separated and the solvent is distilled under reduced pressure (20 mmHg) at 35° C. until no more solvent passes over. The pressure is then lowered to 3 mmHg and the external temperature is raised up to 300° C. and the fraction that distils between 255° C. and 265° C., (40.6 g), is collected.

A GC analysis shows a area/area ratio of C,O-dibenzylated derivative (Va) of the title compound vs. the monoalkylated one (IVa) of 99.6:0.4. (area/area, see Example 16A).

$^1$H-NMR (CDCl$_3$) (Bruker AV300) δ (ppm, with respect to TMS): 4.05 (2H, s, CH$_2$); 5.13 (2H, s, OCH$_2$); 6.85-7.40 (9H, m, aromatic H); 7.73-7.79 (2H, m, aromatic H ortho to C=O); 9.88 (s, CHO).

$^{13}$C-NMR (CDCl$_3$) (Bruker AV300) δ (ppm): 36.1 (CH2); 69.4 (CH2O); 111.4 (aromatic CH); 112.9 and 113.2 (d, $J_{C-F}$=20 Hz, aromatic CH), 113.9 and 114.2 (d, $J_{C-F}$=22 Hz, aromatic CH); 114.9 and 115.0 (d, $J_{C-F}$=21 Hz, aromatic CH; 115.7 e 115.9 (d, $J_{C-F}$=25 Hz aromatic CH); 122.6 (d, $J_{C-F}$=3 Hz, aromatic CH); 124.4 (d, $J_{C-F}$=3 Hz, aromatic CH); 129.6 and 129.8 (d, $J_{C-F}$=8 Hz, aromatic CH); (d, $J_{C-F}$=7 Hz, quaternary aromatic C); 129.9 (C quaternary aromatic C); 130.0 (quaternary aromatic C); 130.1 and 130.2 (d, $J_{C-F}$ 7 Hz, CH aromatic); 131.2 (aromatic CH); 131.5 (aromatic CH); 138.3 (d, $J_{C-F}$=7 Hz, quaternary aromatic C); 142.3 (d, $J_{C-F}$=7 Hz, quaternary aromatic C); 161.0, 161.2 and 164.4 (d, $J_{C-F}$=240, 2 C-F overlapping); 190.8 (CHO).

b) (S)-2-[3-(3-Fluorobenzyl)-4-(3-fluorobenzyloxy)-benzylamino]propanamide (IIa)

To 3-(3-fluorobenzyl)-4-(3-fluorobenzyloxy)benzaldehyde (35.6 g, 0.105 mol) in a 500 mL flask, a solution previously prepared by cautiously adding under stirring triethylamine (12 g, 0.119 mol) to a 170 mL methanol solution of L-alaninamide hydrochloride (14.8 g, 0.119 mol), is added at room temperature. This reaction mixture is stirred for 1 hour at room temperature and then it is transferred to a 1.8 L autoclave and additioned of 3.4 g of wet (50% H$_2$O) Pt/C 5%.

The air is purged from the autoclave with nitrogen and then hydrogen is introduced at 5.0 bar.

The reaction is performed at a temperature of 35° C. for 3-5 hours.

After cooling to room temperature and eliminating the catalyst by filtration, the solvent is distilled off under reduced pressure until a residue of approximately 65 g is obtained. To this residue a mixture of ethylacetate (340 mL) and water (250 mL) is added and the heterogeneous mixture is warmed to 40° C. and kept at this temperature without stirring, until two clear phases are obtained. The two phases are separated and the organic one is distilled under reduced pressure, until a residue of approximately 50 g is obtained. This residue is dissolved in 220 mL of ethyl acetate and the solvent distilled off under reduced pressure with an external temperature of 40° C. This operation is repeated twice and the title compound is obtained as solid residue.

c) (S)-2-[3-(3-Fluorobenzyl)-4-(3-fluorobenzyloxy)-benzylamino]propanamide methanesulfonate (IIc)

In a 2 L glass reactor 42.4 g (0.103 mol) of (S)-3-(3-fluorobenzyl)-4-(3-fluorobenzyloxy)-benzylamino]propanamide base are dissolved in 950 mL of ethyl acetate.

The solution is heated under stirring at 50-55° C. and kept at this temperature for one hour. To this solution, 14.5 g (0.15 mol) of methanesulfonic acid are added in 20 minutes, and the temperature is lowered to 20° C. in 90 minutes. After 30 minutes the solid is collected by filtration, dried at 50° C. under reduced pressure and then crystallized from methanol (methanol: product 1:5 by weight) to obtain 25.1 g of (S)-2-[3-(3-fluorobenzyl)-4-(3-fluorobenzyloxy)-benzylamino] propanamide methanesulfonate, m. p. 181° C. (capillary).

$^1$H-NMR (DMSO-d$_6$) (Bruker AV300) δ (ppm, with respect to TMS): 1.44 (3H, d, J=7 Hz, CH$_3$); 2,35 (3H, s, CH3SO$_3$); 3,81 (1H, q, J=7 Hz, H-2), 3.99 (2H, bs, CH$_2$ benzylic); 4.02 (2H, AB system, CH$_2$N—); 5.17 (2H, s, CH$_2$OR); 6.98-7.63 (11H, m, aromatic H); 7.62 and 7.75 (2H, bs, NH$_2$ amide); 9.02 (2H, broad, NH2$^+$).

$^{13}$C-NMR (DMSO-d$_6$) (Bruker AV300) δ (ppm): 15.9 (CH$_3$); 35.5 (CH$_2$); 39.7 (CH$_3$SO$_3$H); 48.1 (CH$_2$NR); 54.4 (CH); 68.4 (OCH$_2$); 112.2 (aromatic CH); 112.7 (d, $J_{C-F}$=22 Hz, aromatic CH); 113.8 (d, $J_{C-F}$=22 Hz, aromatic CH); 114.5 (d, $J_{C-F}$=22 Hz, aromatic CH); 115.2 (d, $J_{C-F}$=22 Hz, aromatic CH); 123.2 (aromatic CH); 123.8; 124.6 (aromatic CH); 128.7 and 130.0 (d, $J_{C-F}$=6 Hz, aromatic CH); 130.04 (aromatic CH); 130.3 (d, $J_{C-F}$=6 Hz, aromatic CH); 132.6 (aromatic CH); 139.8 (d, $J_{C-F}$=7 Hz); 143.4 (d, $J_{C-F}$=7 Hz); 158.1, 160.5 and 163.7 (d, $J_{C-F}$=240, C—F); 160.6 and 163.8 (d, $J_{C-F}$=240, C—F); 170.5 (CON). A sample (90 mg) of (S)-2-[3-(3-fluorobenzyl)-4-(3-fluorobenzyloxy)-benzylamino]propanamide (IIa) is isolated also by preparative HPLC from a 200 g of safinamide methanesulfonate (Ic) prepared according to J. Med. Chem., 1998, 41, 579, method A, that contains it, as methanesulfonate (IIc), in 0.12% by weight.

The separation is performed, in two stages (Stage 1 and Stage2), according to the following scheme:

Isolation of IIa by preparative HPLC of safinamide methanesulfonate (Ic) contaminated by 0.12% by weight of IIc
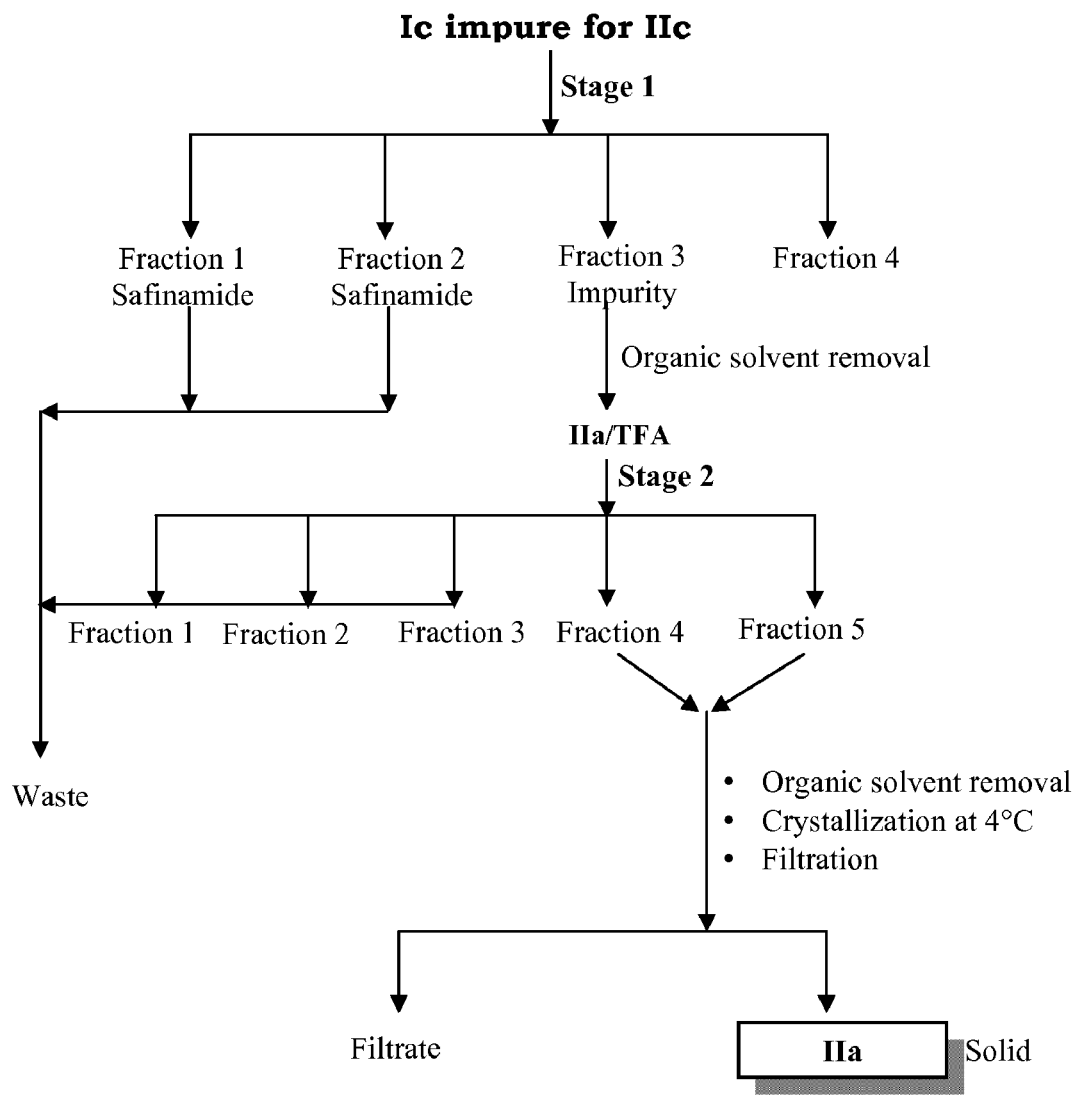

Stage 1

The scope of the first stage is to isolate a crude product enriched in IIa/TFA (Trifluoroacetic acid).

Preparative HPLC conditions are reported below:

Preparative HPLC Conditions:
- Instrument: Waters Delta Prep 4000 (reciprocating pump, gradient controller with low pressure mixer)
  Radial Compression Module Prep LC Base (Waters)
  Jasco 7125 UV-Variable detector, o.p. 0.2 mm
  Merk D2000 printer-plotter
- Column: Delta Pak C18, 15 μm, 40×100 mm (Waters)
- Eluent A: 70/30, Water/Acetonitrile+0.1% TFA
- Eluent B: 30/70, Water/Acetonitrile+0.1% TFA
- Flow rate: 27.0 ml/min
- Gradient: 40 min, isocratic 100% A, then to 100% B in 1 minute
- Detection: UV 227 nm
- Injection: 5 g in 50 ml of Water (by pump inlet line D)

Stage 2

This stage is needed to eliminate TFA from IIa/TFA and to further purify IIa. IIa/TFA is chromatographed using the preparative HPLC conditions given below.

The fraction 4 and 5 are combined together and evaporated at 40° C. under vacuum until complete removal of acetonitrile. The residual water solution is kept in a refrigerator at 4° C. The insoluble is isolated by filtration and dried under vacuum at room temperature to provide IIa (90 mg; HPLC purity 100%).

Preparative HPLC Conditions:
- Instrument: Waters Delta Prep 4000 (reciprocating pump, gradient controller with low pressure mixer)
  Jasco 7125 UV-Variable detector, o.p. 0.2 mm
  Merk D2000 printer-plotter
- Column: Symmetry C18, 7 μm, 20×250 mm (Waters)
- Eluent A: 70/30, Water/Acetonitrile
- Eluent B: 30/70, Water/Acetonitrile
- Flow rate: 15.0 ml/min
- Gradient: 20 min, isocratic 100% A, then to 100% B in 10 minutes
- Detection: UV 227 nm
- Injection: 50 ml of impurity "IIa/TFA" solution (by pump inlet line D)

Example 11

Preparation of (S)-2-[3-(2-fluorobenzyl)-4-(2-fluorobenzyloxy)-benzylamino]propanamide methanesulfonate (IId)

a) 3-(2-Fluorobenzyl)-4-(2-fluorobenzyloxy)benzaldehyde (Vb)

3-(2-Fluorobenzyl)-4-(2-fluorobenzyloxy)benzaldehyde is prepared by following the same procedure of Example 10, step a) in a 1:10 scale, but using 2-fluorobenzyl chloride instead of 3-fluorobenzyl chloride. The molar yield is 3% with a 98.1 purity determined by GC analysis (area %, see Example 16A). The product has m.p. 71° C. (capillary).

$^1$H-NMR: (CDCl$_3$, 300 MHz, 298K) δ (ppm, with respect to TMS): 4.06 (2H, s, CH$_2$); 5.23 (2H, s, OCH$_2$); 6.95-7.40 (9H, m, aromatic H); 7.67 (1H, bd, J=0.9 Hz, aromatic H ortho to C=O and CH$_2$); 7.76 (1H, dd, J$_1$=2.1 Hz, J$_2$=8.3 Hz, aromatic H ortho to C=O and aromatic CH); 9.84 (1H, s, CHO).

$^{13}$C-NMR: (CDCl$_3$, 75.4 MHz, 298K) δ (ppm): 29.2 (CH$_2$); 64.1 (OCH$_2$); 111.4 (aromatic CH); 115.4 (d, J$_{C-F}$=22.0 Hz, aromatic CH), 115.5 (d, J$_{C-F}$=21.1 Hz, aromatic CH); 123.3 (d, J$_{C-F}$=14.2 Hz, quaternary aromatic C); 124.1 (d, J$_{C-F}$=2.6 Hz, aromatic CH); 124.5 (d, J$_{C-F}$=3.2 Hz, aromatic CH); 126.6 (d, J$_{C-F}$=15.5 Hz, quaternary aromatic C); 128.2 (d, J$_{C-F}$=8.1 Hz, aromatic CH); 129.6 (d, J$_{C-F}$=6.2 Hz, aromatic CH); 129.6 (quaternary aromatic C); 130.0 (quaternary aromatic C); 130.2 (d, J$_{C-F}$=8.3 Hz, aromatic CH); 131.1 (aromatic CH); 131.3 (d, J$_{C-F}$=4.1 Hz, aromatic CH); 131.8 (aromatic CH); 160.5 (d, J$_{C-F}$=246.8 Hz, quaternary aromatic C); 161.2 (d, J$_{C-F}$=245.1 Hz, quaternary aromatic C); 161.3 (quaternary aromatic C); 191.1 (CHO).

b) (S)-2-[3-(2-Fluorobenzyl)-4-(2-fluorobenzyloxy)-benzylamino]propanamide (IIb)

(S)-2-[3-(2-Fluorobenzyl)-4-(2-fluorobenzyloxy)benzylamino]-propanamide is prepared by following the same procedure of Example 10, step b) by using 3-(2-fluorobenzyl)-4-(2-fluorobenzyloxy)benzaldehyde instead of 3-(3-fluorobenzyl)-4-(3-fluorobenzyloxy)benzaldehyde. The yield is 83%; m.p. 161° C. (capillary).

$^1$H-NMR: (CDCl$_3$, 300 MHz, 298K) δ (ppm, with respect to TMS): 1.32 (3H, d, J=6.7 Hz, CH$_3$); 1.97 (1H, bs, NH); 3.22 (1H, q, J=6.7 Hz, CH—CO); 3.67 (2H, ABq, J=12.8 Hz, diastereotopic H of NCH$_2$); 4.03 (2H, s, CH$_2$); 5.12 (2H, s, OCH$_2$); 5.98 (1H, bs, NH$_2$); 6.89 (1H, d, J$_{orto}$=8.3 Hz, aromatic H ortho to CH$_2$NH and aromatic CH); 6.95-7.40 (10H, m, aromatic H).

$^{13}$C-NMR: (CDCl$_3$, 75.4 MHz, 298K) δ (ppm): 19.6 (CH$_3$); 29.2 (CH$_2$); 52.0 (NHCH$_2$); 57.7 (H$_2$NCOCH); 63.8 (OCH$_2$); 111.7 (aromatic CH); 115.2 (d, J$_{C-F}$=21.9 Hz, aromatic CH), 115.3 (d, J$_{C-F}$=21.3 Hz, aromatic CH); 124.0 (d, J$_{C-F}$=3.5 Hz, aromatic CH); 124.3 (d, J$_{C-F}$=2.9 Hz, aromatic CH); 124.3 (d, J$_{C-F}$=14.4 Hz, quaternary aromatic C); 127.5 (aromatic CH); 127.6 (d, J$_{C-F}$=15.0 Hz, quaternary aromatic C); 127.8 (d, J$_{C-F}$=7.5 Hz, aromatic CH); 128.8 (quaternary aromatic C); 129.0-130.0 (m, 2 aromatic CH); 130.5 (aromatic CH); 131.3 (d, J$_{C-F}$=4.6 Hz, aromatic CH); 131.8 (quaternary aromatic C); 155.6 (quaternary aromatic C); 160.4 (d, J$_{C-F}$=245.8 Hz, quaternary aromatic C); 161.2 (d, J$_{C-F}$=244.6 Hz, quaternary aromatic C); 178.2 (CONH$_2$).

c) (S)-2-[3-(2-Fluorobenzyl)-4-(2-fluorobenzyloxy)-benzylamino]propanamide methanesulfonate (IId)

(S)-2-[3-(2-Fluorobenzyl)-4-(2-fluorobenzyloxy)-benzylamino]propanamide methanesulfonate is prepared by following the same procedure of Example 10, step c) but using (S)-2-[3-(2-fluorobenzyl)-4-(2-fluorobenzyloxy)-benzylamino]propanamide as the starting material. The yield is 89%; m.p. 190° C. (capillary).

$^1$H-NMR: (DMSO-d$_6$, 300 MHz, 298K) δ (ppm, with respect to TMS): 1.42 (3H, d, J=6.8 Hz, CH$_3$CH); 2.33 (3H, s, CH$_3$SO$_3$); 3.50-4.20 (5H, m, CH—CO, CH$_2$, diastereotopic H of NCH$_2$,); 5.19 (2H, s, OCH$_2$); 6.95-8.00 (11H, m, aromatic H); 9.02 (2H, bs, NH$_2$+).

$^{13}$C-NMR: (DMSO-d$_6$, 75.4 MHz, 298K) δ (ppm): 16.5 (CH3); 28.8 (CH$_2$); 48.6 (NHCH$_2$); 54.9 (H$_2$NCOCH); 64.3 (OCH$_2$); 112.8 (aromatic CH); 115.0-117.0 (2 aromatic CH); 124.2 (d, J$_{C-F}$=14.4 Hz, quaternary aromatic C); 124.4 (quaternary aromatic C); 124.8 (aromatic CH); 125.0 (aromatic CH); 127.3 (d, J$_{C-F}$=16.1 Hz, quaternary aromatic C); 128.6 (quaternary aromatic C); 128.8 (aromatic CH); 129.0-133.0 (m, 5 aromatic CH); 156.9 (quaternary aromatic C); 160.8 (d, J$_{C-F}$=245.2 Hz, quaternary aromatic C); 160.9 (d, J$_{C-F}$=243.5 Hz, quaternary aromatic C); 171.1 (CONH$_2$).

Example 12

Preparation of (S)-2-[4-3-fluorobenzyloxy)benzylamino]propanamide (safinamide) methanesulfonate (Ic) from 4-(3-fluorobenzyloxy)benzaldehyde (IVa) contaminated by 1% by weight of impurity 3-(3-fluorobenzyl)-4-(3-fluorobenzyloxy)benzaldehyde (Va)

To 4-(3-fluorobenzyloxy)benzaldehyde (10 g; GC purity 98.8, area %), 1% of 3-(3-fluorobenzyl)-4-(3-fluorobenzyloxy)benzaldehyde is added and the mixture is converted into (S)-2-[4-(3-fluorobenzyloxy)benzylamino]propanamide safinamide base by following the same procedure of Example 6. The yield is 84% with a content of impurity (IIa) of 0.84% (see Example 17B) by weight. The free base (S)-2-[4-(3-fluorobenzyloxy)benzylamino]propanamide (Ia) is converted into the corresponding methanesulphonate by following the same procedure of Example 7 to provide the methanesulphonate (Ic) in 98% yield with a content of impurity (S)-2-[3-(3-fluorobenzyl)-4-(3-fluorobenzyloxy)-benzylamino]propanamide methanesulfonate (IIc) of 0.62% by weight determined by HPLC (see Example 17B).

Example 13

Crystallization of Safinamide Methanesulfonate (Ic) Contaminated by Impurity (IIc)

The safinamide methanesulfonate contaminated by (S)-2-[3-(3-fluorobenzyl)-4-(3-fluorobenzyloxy)-benzylamino] propanamide methanesulfonate (IIc) of 0.62% by weight determined by HPLC (see Example 17B) obtained according to Example 12, is crystallized by using five different(s) solvent systems by dissolving at reflux temperature and cooling at room temperature.

The result are reported in the following Table 5

TABLE 5

| TEST No. | SOLVENT SYSTEM AND AMOUNT (mL/g) | % w/w of IIc in Ic after crystallization (*) | % Molar Yield |
| --- | --- | --- | --- |
| 13a | 2-PrOH/MeOH 2:1, 45 | 0.28 | 44.9 |
| 13b | EtOAc/MeOH 4:1, 50 | 0.15 | 29.6 |
| 13c | EtOH, 10 | 0.30 | 73.2 |
| 13d | Acetone/H$_2$O ~27:1, 40.5 | 0.08 | 20.6 |
| 13e | Acetonitrile/H$_2$O 60:1, 30.5 | 0.09 | 69.3 |

(*) the % (w/w) is evaluated according to Example 17B.

Example 14

Preparation of (S)-2-[4-(3-fluorobenzyloxy)benzylamino]propanamide (safinamide, Ia) methanesulfonate (Ic) according to known methods

14.1 Preparation of 4-(3-fluorobenzyloxy)benzaldehyde (IVa)

14.1.a) Procedure of Example 1a of U.S. Pat. No. 6,335,354 B2

4-(3-Fluorobenzyloxy)benzaldehyde (IVa) is prepared by the procedure described in Example 1a of U.S. Pat. No. 6,335,354 B2.

Accordingly, a mixture of 3-fluorobenzyl chloride (2.86 g, 19.80 mmol) 4-hydroxybenzaldehyde (3.03 g, 24.80 mmol), K$_2$CO$_3$ (10.30 g, 74.50 mmol), NaI (137.1 mg, 0.91 mmol), and ethanol, (40 mL) is heated to reflux in 70 minutes and kept at reflux temperature for 4 hours and 15 minutes.

After working up the reaction mixture, 4-(3-fluorobenzyloxy)benzaldehyde, is isolated as a yellow oil in 95% yield.

The product has GC purity of 97.6 (area %, see Example 16A) and a content of 3-(3-fluorobenzyl)-4-(3-fluorobenzyloxy)benzaldehyde (Va) of 0.14% by weight determined by GC (see Example 16B)

14.1.b) Procedure of J. Agric. Food Chem, 27, 4, 1979

4-(3-Fluorobenzyloxy)benzaldehyde (IVa) is prepared by the procedure reported in J. Agric. Food Chem, 27, 4, 1979.

Accordingly, 3-fluorobenzyl chloride (14.5 g, 100 mmol) is added under stirring and under nitrogen atmosphere to a solution of 4-hydroxybenzaldehyde (12.2 g, 100 mmol) and of NaOH (4.0 g, 100 mmol) in ethanol (100 mL).

The mixture is gradually heated in 25 minutes to reflux and stirred at reflux temperature for 6 hours and 20 minutes. The reaction mixture is filtrated and then concentrated at reduced pressure to obtain 4-(3-fluoro-benzyloxy)benzaldehyde (23.43 g) as a yellow solid residue. Dichloromethane (250 mL) is added to the residue, the insoluble is filtered and the resulting solution is concentrated under reduced pressure to provide 4-(3-fluorobenzyloxy)benzaldehyde as a yellow solid, in 80.4% yield.

The product has GC purity of 91.6 (area %, see Example 16A) and a content of 3-(3-fluorobenzyl)-4-(3-fluorobenzyloxy)benzaldehyde (Va) of 0.13% by weight determined by GC(see Example 16B)

14.2 Preparation of (S)-2-[4-(3-fluorobenzyloxy)benzylamino]propanamide (Ia) and its methanesulfonate salt (Ic)

14.2.a) Procedure of J. Med. Chem., 1998, 41, 579, Method A (S)-2-[4-(3-Fluorobenzyloxy)benzylamino]propanamide (Ia) is prepared by reacting 4-(3-fluorobenzyloxy)benzaldehyde (10 mmol), prepared as described in Example 14.1.a., and L-alaninamide hydrochloride (1.37 g, 11 mmol) followed by reduction with NaBH$_3$CN (0.50 g, 8 mmol). After working up the reaction mixture and purification by flash-chromatography, (S)-2[4-(3-fluorobenzyloxy)benzylamino]propanamide is isolated as white solid in 68.7% yield. The product has HPLC purity of 96.2 (area %, see Example 17A) and a content of (S)-2-[3-(3-fluorobenzyl)-4-(3-fluorobenzyloxy)-benzylamino]propanamide (IIa) of 0.15% by weight (see Example 17B).

A mixture of (S)-2[4-(3-fluorobenzyloxy)benzylamino] propanamide (1.50 g, 4.96 mmol) and ethyl acetate (40.2 mL) is heated to 50° C. until a clear solution is obtained. Methanesulfonic acid (0.53 g, 5.51 mmol) is added under stirring in 15 minutes to the solution and the resulting heterogeneous mixture is cooled under stirring to 20° C. in 90 minutes. After 30 minutes at 20° C. the solid is collected by filtration, washed with ethyl acetate (6 mL) and dried at 50° C. at reduced pressure for 15 hrs to provide (S)-2[4-(3-fluorobenzyloxy) benzylamino]propanamide methanesulfonate (Ic) as a white solid in a 96.1% yield. The product has HPLC purity 98.6 (area %, see Example 17A) and a content of (S)-2-[3-(3-fluorobenzyl)-4-(3-fluorobenzyloxy)-benzylamino]propanamide methanesulfonate (IIc) of 0.10% by weight determined by HPLC (see Example 17B).

14.2.b) Procedure of J. Med. Chem., 1998, 41, 579, Method A (S)-2-[4-(3-Fluorobenzyloxy)benzylamino]propanamide (Ia) is prepared according to example 14.2.a from 4-(3-fluorobenzyloxy)benzaldehyde (10 mmol), prepared as described in example 14.1.b., and L-alaninamide hydrochloride (1.37 g, 11 mmol) followed by reduction with NaBH$_3$CN (0.50 g, 8 mmol).

(S)-2-[4-(3-fluorobenzyloxy)benzylamino]propanamide (Ia), is obtained as white solid in 66.5% yield. The product has HPLC purity of 88.5 (area %, see Example 17A) and a content of (S)-2-[3-(3-fluorobenzyl)-4-(3-fluorobenzyloxy)-benzylamino]propanamide (IIa) of 0.064% by weight determined by HPLC (see Example 17B). (S)-2-[4-(3-Fluorobenzyloxy)benzylamino]propanamide (Ia) is converted into the corresponding methanesulfonate (Ic) in a 88.9% yield by treatment with methanesulfonic acid according to Example 14.2.a. The product has a HPLC purity of 97.7 (area %, see Example 17A) and a content of (S)-2-[3-(3-fluorobenzyl)-4-(3-fluorobenzyloxy)-benzylamino]propanamide methanesulfonate (IIc) of 0.05% by weight determined by HPLC (see Example 17B).

Example 15

Preparation of (S)-2-[4-(2-fluorobenzyloxy)benzylamino]propanamide (ralfinamide, Ib) methanesulfonate (Id) according to known methods 15.1 Preparation of 4-(2-fluorobenzyloxy)benzaldehyde (IVb)

15.1.a) Procedure of Example 1a of U.S. Pat. No. 6,335,354 B2

4-(2-Fluorobenzyloxy)benzaldehyde (IVb) is prepared according to the Example 14.1.a) from 2-fluorobenzyl chloride (14.3 g, 98 mmol), 4-hydroxybenzaldehyde (15.1 g, 123 mmol), K$_2$CO$_3$ (51 g, 369 mmol), NaI (500 mg, 3.3 mmol.) ethanol, 75 mL.

The mixture is kept at reflux for 12 hrs. After working up the reaction mixture, 4-(2-fluorobenzyloxy)benzaldehyde is obtained in 75% yield as a yellow oil. The product has GC purity of 92.1 (area %, see Example 16A) and a content of 3-(2-fluorobenzyl)4-(2-fluorobenzyloxy)benzaldehyde of 0.25% by weight determined by G.C. (see Example 16B).

15.1.b) Procedure of J. Agric. Food Chem, 27, 4, 1979

4-(2-Fluorobenzyloxy)benzaldehyde (IVb) is prepared according to Example 14.1.b from 2-fluorobenzyl chloride (18.0 g, 123 mmol), 4-hydroxy-benzaldehyde (15.3 g, 125 mmol), NaOH (5.0 g, 12 mmol) and ethanol (125 mL).

The mixture is heated in 25 minutes to reflux and kept at reflux temperature under stirring for 12 hours.

After working up the reaction mixture according to Example 14.1.b 4-(2-fluorobenzyloxy)benzaldehyde is obtained as a yellow solid, in 90.0% yield. The product has GC purity of 90.4 (area %, see Example 16A) and a content of 3-(2-fluorobenzyl)-4-(2-fluorobenzyloxy)benzaldehyde (Vb) of 0.14% by weight determined by G.C. (see Example 16B).

15.2 Preparation of (S)-2-[4-(2-fluorobenzyloxy) benzylamino]propanamide (Ib) and its methanesulfonate salt (Id)

15.2.a) Procedure of J. Med. Chem, 1998, 41, 579, Method A (S)-2-[4-(2-Fluorobenzyloxy)benzylamino]propanamide (Ib) is prepared following the procedure of Example 14.2.a by using 4-(2-fluorobenzyloxy)benzaldehyde (10 mmol, prepared as in Example 15.1 a) instead of 4-(3-fluorobenzyloxy) benzaldehyde.

(S)-2[4-(2-Fluorobenzyloxy)benzalamino]propanamide is obtained in 67.3% yield as a white solid. The product has a HPLC purity of 86.7 (area %, see Example 17A) and a content of (S)-2-[3-(2-fluorobenzyl)-4-(2-fluorobenzyloxy)-benzylamino]propanamide (IIb) of 0.22% by weight determined by HPLC (see Example 17B).

A mixture of (S)-2[4-(2-fluorobenzyloxy)benzylamino] propanamide (1.50 g, 4.96 mmol) and propan-2-ol (10.5 mL) is heated to 50° C. and kept at this temperature until a clear solution is obtained. Methanesulfonic acid, (0.48 g, 5.01 mmol) is added under stirring in 15 minutes.

The heterogeneous mixture is then cooled under stirring to 20° C. in 2 hours. After 1 hour at 20° C. the solid is collected by filtration, dried at reduced pressure to provide (S)-2[4-(2-fluorobenzyloxy)benzylamino]propanamide methanesulfonate as white solid in 89.1% yield. The product has a HPLC purity of 96.9 (area %, see Example 17A) and a content of (S)-2-[3-(2-fluorobenzyl)-4-(2-fluorobenzyloxy)benzylamino]propanamide methanesulfonate (IId) of 0.14% by weight determined by HPLC (see Example 17B).

15.2.b) Procedure of J. Med. Chem. 1998, 41, 579, Method A (S)-2-[4-(2-Fluorobenzyloxy)benzylamino]propanamide (Ib) is prepared according to Example 14.2.b by using 4-(2-fluorobenzyloxy)benzaldehyde (10 mmol, prepared according to Example 15.1.b) instead of 4-(3-fluorobenzyloxy)benzaldehyde.

(S)-2-[4-(2-Fluorobenzyloxy)benzylamino]propanamide is obtained as a white solid in 58.8% yield. The product has a HPLC purity 83.8 (area %, see Example 17A) and a content of (S)-2-[3-(2-fluorobenzyl)-4-(2-fluorobenzyloxy)-benzylamino]propanamide (IIb) of 0.15% by weight determined by HPLC (see Example 17B).

(S)-2-[4-(2-fluorobenzyloxy)benzylamino]propanamide (Ib) is converted into the corresponding methanesulfonate (Id) in a 89.4% yield as a white solid. The product has a HPLC purity of 95.2 (area %, see Example 17A) and a content of (S)-2-[3-(2-fluorobenzyl)-4-(2-fluorobenzyloxy)-benzylamino]propanamide methanesulfonate of 0.11% by weight determined by HPLC (see Example 17B).

Example 16A

GC determination of 4-(3-fluorobenzyloxy)benzaldehyde and 4-(2-fluorobenzyloxy)benzaldehyde purity Test Preparation Dissolve about 100 mg of the sample in 10 ml of methylene chloride. Chromatographic conditions The chromatographic procedure is carried out by using:
- a fused silica capillary column 60 m long and 0.32 mm internal diameter. RTX 35 (35% Diphenyl-65% Dimethyl polysiloxane) Film thickness=0.25 μm;
- helium as carrier gas at a pressure of 150 kPa;
- a split flow of 25 ml/min;
- injector temp. 290° C.;
- detector (FID) temp. 290° C.;

with the following temperature program:

| Time (min) | Temperature (° C.) | Rate (° C./min) | Comment |
|---|---|---|---|
| 0-5 | 150 | — | isothermal |
| 5-11 | 150→240 | 15 | linear gradient |
| 11-19 | 240 | — | isothermal |
| 19-20.7 | 240→290 | 30 | linear gradient |
| 20.7-40 | 290 | — | isothermal |

Procedure

Inject 1 μl of the Test Preparation. Record the chromatogram and calculate the product purity by area percent calculation.

Impurities Identification 4-(3-Fluorobenzyloxy)benzaldehyde (IVa):

Retention Times:

4-(3-Fluorobenzyloxy)benzaldehyde retention time is about 17.

4-Hydroxybenzaldehyde relative retention time is about 0.52.

4-(2-Fluorobenzyloxy)benzaldehyde relative retention time is about 0.98.

4-(4-Fluorobenzyloxy)benzaldehyde relative retention time is about 1.01.

4-Benzyloxybenzaldehyde relative retention time is about 1.02.

3-(3-Fluorobenzyl)-4-(3-fluorobenzyloxy)benzaldehyde relative retention time is about 1.78.

4-(2-Fluorobenzyloxy)benzaldehyde (IVb):

Retention Times:

4-(2-Fluorobenzyloxy)benzaldehyde retention time is about 17.

4-Hydroxybenzaldehyde relative retention time is about 0.53.

4-(3-Fluorobenzyloxy)benzaldehyde relative retention time is about 1.02.

4-(4-Fluorobenzyloxy)benzaldehyde relative retention time is about 1.03.

4-Benzyloxybenzaldehyde relative retention time is about 1.04.

3-(2-Fluorobenzyl)-4-(2-fluorobenzyloxy)benzaldehyde relative retention time is about 1.81.

Example 16B

GC determination of the content of 3-(2-fluorobenzyl)-4-(2-fluorobenzyloxy)benzaldehyde (Vb) in 4-(2-fluorobenzyloxy) benzaldehyde (IVb) and of 3-(3-fluorobenzyl)-4-(3-fluorobenzyloxy) benzaldehyde (Va) in 4-(3-fluorobenzyloxy)benzaldehyde (IVa)

The known related substance taken into consideration for 4-(2-fluorobenzyloxy)benzaldehyde is the 3-(2-fluorobenzyl)-4-(2-fluorobenzyloxy)benzaldehyde and for 4-(3-fluorobenzyloxy)benzaldehyde is the 3-(3-fluorobenzyl)-4-(3-fluorobenzyloxy)benzaldehyde. The determination is carried out according to the following conditions:

Internal Standard Solution

Prepare a 3,4,5-trimethoxybenzaldehyde solution with concentration 1.5 mg/ml in methylene chloride (IS).

Reference solution for the 3-(2-fluorobenzyl)-4-(2-fluorobenzyloxy) benzaldehyde determination in the 4-(2-fluorobenzyloxy)benzaldehyde Accurately weigh about 20 mg of 3-(2-fluorobenzyl)-4-(2-fluorobenzyloxy)benzaldehyde reference standard and 20 mg of 4-(2-fluorobenzyloxy)benzaldehyde reference standard in a 20 mL volumetric flask, dissolve and dilute to volume with diluent; transfer 500 μL of this solution in a 5 mL volumetric flask, add 500 μL of IS solution and dilute to volume with diluent to obtain a solution containing 3-(2-fluorobenzyl)-4-(2-fluorobenzyloxy)benzaldehyde and 4-(2-fluorobenzyloxy)benzaldehyde at about 100 μg/mL (corresponding to about 0.10%).

Reference solution for the 3-(3-fluorobenzyl)-4-(3-fluorobenzyloxy) benzaldehyde determination in the 4-(3-fluorobenzyloxy)benzaldehyde Accurately weigh about 20 mg of 3-(3-fluorobenzyl)-4-(3-fluorobenzyloxy)benzaldehyde reference standard and 20 mg of 4-(3-fluorobenzyloxy)benzaldehyde reference standard in a 20 mL volumetric flask, dissolve and dilute to volume with diluent; transfer 500 μL of this solution in a 5 mL volumetric flask, add 500 μL of IS solution and dilute to volume with diluent to obtain a solution containing 3-(3-fluorobenzyl)-4-(3-fluorobenzyloxy)benzaldehyde and 4-(3-fluorobenzy-loxy)benzaldehyde at about 100 μg/mL (corresponding to about 0.10%).

Test Solution:

Accurately weigh about 500 mg of test product in a 5 mL volumetric flask, add 500 μL of IS solution, dissolve and dilute to volume with diluent to obtain a solution having known concentration of about 100 mg/mL.

Chromatographic Conditions:

The chromatographic procedure is carried out by using:
- Column: a fused silica capillary column RTX 35 (35% Diphenyl-65% Dimethyl polysiloxane) 60 m long, 0.32 mm I.D., film thickness 0.25 μm;
- Carrier (helium) at pressure of 150 kPa;
- Split flow 25 mL/min;
- Injector temp. 290° C.;
- Detector (FID) temp. 290° C.;
- Temperature program: 0-5 min isothermal at 150° C., 5-11 min linear from 150° C. to 240° C. at a rate of 15° C./min, 11-19 min isothermal at 240° C., 19-21 min linear from 240° C. to 290° C. at a rate of 30° C./min, 21-40 min isothermal at 290° C.;

diluent: methylene chloride
injection volume 1 μL.
Procedure:
Inject blank (diluent), reference solution, test solution and record the chromatograms.
In the reference chromatogram verify that:
4-(2-Fluorobenzyloxy)benzaldehyde retention time is about 18 min;
3-(2-Fluorobenzyl)-4-(2-fluorobenzyloxy)benzaldehyde relative retention time is about 1.7
or
4-(3-Fluorobenzyloxy)benzaldehyde retention time is about 18 min;
3-(3-Fluorobenzyl)-4-(3-fluorobenzyloxy)benzaldehyde relative retention time is about 1.7
3,4,5-Trimethoxybenzaldehyde (IS) relative retention time is about 0.7

Calculate the percent content of 3-(2-fluorobenzyl)-4-(2-fluorobenzyloxy)benzaldehyde in the 4-(2-fluorobenzyloxy)benzaldehyde examined or of the 3-(3-fluorobenzyl)-4-(3-fluorobenzyloxy)benzaldehyde in the 4-(3-fluorobenzyloxy)benzaldehyde examined by internal standard calculation. The value of the limit of quantitation (LOQ) for (3-(2-fluorobenzyl)-4-(2-fluorobenzyloxy)benzaldehyde and of 3-(3-fluorobenzyl)-4-(3-fluorobenzyloxy)benzaldehyde is 0.005% by weight. The value of the limit of detection (LOD) for both considered impurities is 0.0025% by weight.

Example 17A

HPLC determination of purity of (S)-2-[4-(3-fluorobenzyloxy) benzylamino]propanamide (safinamide (Ia)), its methanesulfonate (Ic), (S)-2-[4-(2-fluorobenzyloxy)benzylamino]propanamide (ralfinamide (Ib)) and its methanesulfonate (Id)

The following chromatographic procedure is suitable for both the free base form (Ia, Ib) and the methanesulfonate salt (Ic, Id) of the products.
Diluent
  Mobile phase.
Test Solution
  Accurately weigh about 25 mg of product in a 25 ml volumetric flask, dissolve in and dilute to volume with diluent to obtain a solution having known concentration of about 1.0 mg/ml.
Chromatographic Condition
  The chromatographic procedure is carried out by using:
  Column: Waters Symmetry C8, 150×4.6 mm, 5μ;
  detection: UV 220 nm;
  column temperature: 30° C.
  mobile phase: 40% solvent A+10% solvent B+50% solvent C, containing 1.0 g/l sodium octansulphonate;
    solvent A: Buffer solution=$KH_2PO_4$ 0.05M;
    solvent B: Acetonitrile;
    sovent C: Methanol;
  isocratic elution, run time: 60 minutes;
  flow rate: 1.0 ml/min;
  injection volume: 10 μl.
Procedure
  Inject the test solution, record the chromatogram and calculate the product purity by area percent calculation.

(S)-2-[4-(3-Fluorobenzyloxy)benzylamino]propanamide (safinamide) and related impurities identification Retention Time:
  (S)-2-[4-(3-Fluorobenzyloxy)benzylamino]propanamide retention time is about 5.5 min.
  (S)-2-[4-(3-Fluorobenzyloxy)benzylamino]propionic acid relative retention time is about 0.73.
  (S)-2-[3-(3-Fluorobenzyl)-4-(3-fluorobenzyloxy)-benzylamino]propanamide relative retention time is about 4.08.
  (S)-2-[4-(2-Fluorobenzyloxy)benzylamino]propanamide (ralfinamide) and related impurity identification
Retention Time:
  (S)-2-[4-(2-Fluorobenzyloxy)benzylamino]propanamide retention time is about 5.5 min.
  (S)-2-[4-(2-Fluorobenzyloxy)benzylamino]propionic acid relative retention time is about 0.73.
  (S)-2-[3-(2-Fluorobenzyl)-4-(2-fluorobenzyloxy)-benzylamino]propanamide relative retention time is about 4.08.

Example 17B

HPLC determination of (S)-2-[3-(2-fluorobenzyl)-4-(2-fluorobenzyloxy)benzylamino]propanamide (free base, IIb and methanesulfonate, IId) in (S)-2-[4-(2-fluorobenzyloxy)benzylamino]propanamide (free base, Ib and methanesulfonate, Id) and of (S)-2-[3-(3-fluorobenzyl)-4-(3-fluorobenzyloxy)benzylamino]propanamide (free base, IIa and methanesulfonate, IIc) in (S)-2-[4-(3-fluorobenzyloxy)benzylamino]propanamide (free base, Ia and methanesulfonate, Ic)

The determination of the (S)-2-[3-(2-fluorobenzyl)-4-(2-fluorobenzyloxy)benzylamino]propanamide (free base and methanesulfonate) in (S)-2-[4-(2-fluorobenzyloxy)benzylamino]propanamide (free base and methanesulfonate) samples and of (S)-2-[3-(3-fluorobenzyl)-4-(3-fluorobenzyloxy)benzylamino]propanamide (free base and methanesulfonate) in (S)-2-[4-(3-fluorobenzyloxy)benzylamino]propanamide (free base and methanesulfonate) samples is carried out according to the following conditions:

Reference solution for the (S)-2-[3-(2-fluorobenzyl)-4-(2-fluorobenzyloxy)benzylamino]propanamide determination in the (S)-2-[4-(2-fluorobenzyloxy)benzylamino]propanamide Accurately weigh about 30 mg of (S)-2-[3-(2-fluorobenzyl)-4-(2-fluorobenzyloxy)benzylamino]propanamide methanesulfonate reference standard and 20 mg of (S)-2-[4-(2-fluorobenzyloxy)benzylamino]propanamide reference standard in a 50 mL volumetric flask, dissolve and dilute to volume with diluent; dilute 1.0 mL of this solution to 20 mL with diluent (1$^{st}$ dilution); dilute 1.0 mL of the last solution to 20 mL with diluent (2$^{nd}$ dilution) to obtain a solution containing 2-[3-(2-fluorobenzyl)-4-(2-fluorobenzyloxy)benzylamino]propanamide (about 0.12%) at about 1.20 μg/mL and (S)-2-[4-(2-fluorobenzyloxy)benzylamino]propanamide methanesulfonate at about 1.00 μg/mL (about 0.10%).

Reference solution for the (S)-2-[3-(2-fluorobenzyl)-4-(2-fluorobenzyloxy)benzylamino]propanamide methanesulfonate determination in the (S)-2-[4-(2-fluorobenzyloxy)benzylamino]propanamide methanesulfonate Accurately weigh about 30 mg of (S)-2-[3-(2-fluorobenzyl)-4-(2-fluorobenzyloxy)benzylamino]propanamide methanesulfonate reference standard and 20 mg of (S)-2-[4-(2-fluorobenzyloxy)benzylamino]propanamide methanesulfonate reference standard in a 50 mL volumetric flask, dissolve and dilute to volume with diluent; dilute 1.0 mL of this solution to 20 mL with diluent (1$^{st}$ dilution); dilute 1.0 mL of the last solution to 20 mL with diluent (2$^{nd}$ dilution) to obtain a solution containing 2-[3-(2-fluorobenzyl)-4-(2-fluorobenzyloxy)benzylamino]propanamide (about 0.15% as methanesulfonic salt) at about 1.20 µg/mL and (S)-2-[4-(2-fluorobenzyloxy)benzylamino]propanamide methanesulfonate at about 1.00 µg/mL (about 0.10%).

Reference solution for the (S)-2-[3-(3-fluorobenzyl)-4-(3-fluorobenzyloxy)benzylamino]propanamide in the (S)-2-[4-(3-fluorobenzyloxy)benzylamino]propanamide Accurately weigh about 24 mg of (S)-2-[3-(3-fluorobenzyl)-4-(3-fluorobenzyloxy)benzylamino]propanamide reference standard and 20 mg of (S)-2-[4-(3-fluorobenzyloxy)benzylamino]propanamide reference standard in a 50 mL volumetric flask, dissolve and dilute to volume with diluent; dilute 1.0 mL of this solution to 20 mL with diluent (1$^{st}$ dilution); dilute 1.0 mL of the last solution to 20 mL with diluent (2$^{nd}$ dilution) to obtain a solution containing 2-[3-(3-fluorobenzyl)-4-(3-fluorobenzyloxy)benzylamino]propanamide (about 0.12%) at about 1.20 µg/mL and (S)-2-[4-(3-fluorobenzyloxy)benzylamino]propanamide methanesulfonate at about 1.00 µg/mL (about 0.10%).

Reference solution for the (S)-2-[3-(3-fluorobenzyl)-4-(3-fluorobenzyloxy)benzylamino]propanamide methanesulfonate in the (S)-2-[4-(3-fluorobenzyloxy)benzylamino]propanamide methanesulfonate Accurately weigh about 24 mg of (S)-2-[3-(3-fluorobenzyl)-4-(3-fluorobenzyloxy)benzylamino]propanamide reference standard and 20 mg of (S)-2-[4-(3-fluorobenzyloxy)benzylamino]propanamide methanesulfonate reference standard in a 50 mL volumetric flask, dissolve and dilute to volume with diluent; dilute 1.0 mL of this solution to 20 mL with diluent (1$^{st}$ dilution); dilute 1.0 mL of the last solution to 20 mL with diluent (2$^{nd}$ dilution) to obtain a solution containing 2-[3-(3-fluorobenzyl)-4-(3-fluorobenzyloxy)benzylamino]propanamide (about 0.15% as methanesulfonic salt) at about 1.20 µg/mL and (S)-2-[4-(3-fluorobenzyloxy)benzylamino]propanamide methanesulfonate at about 1.00 µg/mL (about 0.10%).

Test Solution:

Accurately weigh about 25 mg of test product in a 25 mL volumetric flask, dissolve and dilute to volume with diluent to obtain a solution having known concentration of about 1.0 mg/mL.

Chromatographic Conditions:

The chromatographic procedure is carried out by using:
Column: Waters Simmetry C8 150×4.6 mm, 5µ, or equivalent
column temperature: 30° C.
mobile phase: mixture of 40% solvent A: 10% solvent B: 50% solvent C, containing 1 g/lt of sodium octanesulfonate
solvent A: buffer solution 0.05M KH$_2$PO$_4$;
solvent B: acetonitrile;
solvent C: methanol;
isocratic elution;
run time: 60 min;
flow rate: 1.0 mL/min;
detection: UV 220 nm;
injection volume: 100 µl;
diluent: mobile phase Procedure:
Inject blank (diluent), reference solution, test solution and record the chromatograms.

In the reference chromatogram verify the following system suitability parameters:
(S)-2-[4-(2-Fluorobenzyloxy)benzylamino]propanamide retention time is about 5.2 minutes;
The USP tailing for (S)-2-[4-(2-fluorobenzyloxy)benzylamino]propanamide peak is in the range between 0.8 and 1.5;
(S)-2-[3-(2-Fluorobenzyl)-4-(2-fluorobenzyloxy)benzylamino]propanamide relative retention time is about 5.1.

or
(S)-2-[4-(3-Fluorobenzyloxy)benzylamino]propanamide retention time is about 5.5 minutes;
The USP tailing for (S)-2-[4-(3-fluorobenzyloxy)benzylamino]propanamide peak is in the range between 0.8 and 1.5;
(S)-2-[3-(3-Fluorobenzyl)-4-(3-fluorobenzyloxy)benzylamino]propanamide relative retention time is about 4.1.

Adjust the mobile phase in order to obtain the system suitability.

Calculate the percent content (S)-2-[3-(2-fluorobenzyl)-4-(2-fluorobenzyloxy)benzylamino]propanamide (free base and methanesulfonate) in the examined (S)-2-[4-(2-fluorobenzyloxy)benzylamino]propanamide (free base and methanesulfonate) samples and of (S)-2-[3-(3-fluorobenzyl)-4-(3-fluorobenzyloxy)benzylamino]propanamide (free base and methanesulfonate) in the examined (S)-2-[4-(3-fluorobenzyloxy)benzylamino]propanamide (free base and methanesulfonate) samples by external standard calculation.

The value of the limit of quantitation (LOQ) for (S)-2-[3-(2-fluorobenzyl)-4-(2-fluorobenzyloxy)benzylamino]propanamide and for (S)-2-[3-(3-fluorobenzyl)-4-(3-fluorobenzyloxy)benzylamino]propanamide in the corresponding (S)-2-[4-(2-fluorobenzyloxy)benzylamino]propanamide and (S)-2-[4-(3-fluorobenzyloxy)benzylamino]propanamide is 0.004% by weight.

The value of the limit of quantitation (LOQ) for (S)-2-[3-(2-fluorobenzyl)-4-(2-fluorobenzyloxy)benzylamino]propanamide methanesulfonate and for (S)-2-[3-(3-fluorobenzyl)-4-(3-fluorobenzyloxy)benzylamino]propanamide methanesulfonate in the corresponding (S)-2-[4-(2-fluorobenzyloxy)benzylamino]propanamide methanesulfonate and (S)-2-[4-(3-fluorobenzyloxy)benzylamino]propanamide methanesulfonate is 0.005% by weight. The value of the limit of detection for all the considered impurities is 0.001% by weight.

Example 18

HPLC determination of (S)-2-[4-(2-fluorobenzyloxy)benzylamino]propanamide (ralfinamide) methanesulfonate (Id) enantiomeric purity The enantiomeric purity of the sample is evaluated by HPLC. The determination is carried out according to the following:

Standard Solution 1:
Dissolve about 5.3 mg of (R)-2-[4-(2-fluorobenzyloxy)benzylamino]propanamide methanesulfonate reference standard in 25 mL of mobile phase.

Standard Solution 2:

Dissolve about 8.0 mg of (S)-2-[4-(2-fluorobenzyloxy)benzylamino]propanamide methanesulfonate reference standard and 0.2 mL of standard solution 1 in 50 mL of mobile phase.

The concentration of (R)-2-[4-(2-fluorobenzyloxy)benzylamino]propanamide methanesulfonate is about 0.5% calculated with respect to the concentration of (S)-2-[4-(2-fluorobenzyloxy)benzylamino]propanamide methanesulfonate.

Test Solutions 1 and 2:

In duplicate, dissolve about 8.0 mg of the test product in 50 mL of mobile phase.

Chromatographic Conditions:
Column: Chiralpak WH 250 mm×4.6 mm, I.D. 5 µm;
column temperature: 45° C.;
mobile phase: 0.25 mM $CuSO_4$ (accurately weigh about 40 mg of $CuSO_4$ in 1000 mL of water)/MeOH 60/40;
isocratic elution;
flow rate: 1.0 mL/min;
detection: UV 230 nm;
injection volume: 10 µl;
run time: 15 minutes.

Procedure:

Analyse blank (mobile phase) once, standard solution 2 twice, test solutions 1 and 2 once and verify that:
for the standard injections, the RSD % for (R)-2-[4-(2-fluorobenzyloxy)benzylamino]propanamide methanesulfonate percent area is less than 2.0%;
both for standard and sample solutions, for each injection the main peak percent area is included between the average value ±0.1%.

Calculate the (R)-2-[4-(2-fluorobenzyloxy)benzylamino]propanamide methanesulfonate content (percent area) as mean of the two determination.

Retention Times:
(S)-2-[4-(2-Fluorobenzyloxy)benzylamino]propanamide retention time is about 5.7 min.
(R)-2-[4-(2-Fluorobenzyloxy)benzylamino]propanamide relative retention time is about 1.7.

Example 19

HPLC determination of (S)-2-[4-(3-fluorobenzyloxy)benzylamino]propanamide (safinamide) methanesulfonate (Ic) enantiomeric purity The enantiomeric purity of the sample is evaluated by HPLC. The determination takes place according to the following conditions:

Test Solution:

Dissolve about 10 mg of test sample in 10 mL of mobile phase.

Chromatographic Conditions:
Column: Chiralpak WH 250 mm×4.6 mm, I.D. 10 µm;
column temperature: 50° C.;
mobile phase: 0.25 mM $CuSO_4$
isocratic elution;
flow rate: 1.0 mL/min;
detection: UV 200 nm;
injection volume: 10 µl;
run time: 30 minutes.

Procedure:

Inject the test solution and calculate the enantiomers peak response as area percent.

(S)-2-[4-(3-Fluorobenzyloxy)benzylamino]propanamide retention time is about 9.2 min.

(R)-2-[4-(3-Fluorobenzyloxy)benzylamino]propanamide relative retention time is about 1.9.

Example 20

Cytochrome P450 Assay

Inhibition of the five most important Cytochrome P450 isoforms (CYP1A2, CYP2C9, CYP2C19, CYP2D6 and CYP3A4), involved in drug metabolism, was measured using specific substrates that become fluorescent upon CYP metabolism (Gentest Kit assay).

Compounds were tested in a 96-well plate containing incubation/NADPH regenerating buffer. Specific human recombinant isoenzymes and substrates were added and incubated at 37° C. for 15 minutes for CYP1A2/CEC, 40 minutes for CYP2E1/MFC, 45 minutes for CYP2C9/MFC and 30 minutes for the others CYP450.

The specific substrates were the following: 3-cyano-7-ethoxycoumarin (CYP2C19 and CYP1A2),
7-methoxy-4-trifluoromethylcoumarin (CYP2C9),
3[2(N,N-diethyl-N-mwthylamino) ethyl]-7-methoxy-4-methylcoumarin (CYP2D6)
benzylphenylcoumarin (CYP3A4)

The plates were read on a Victor plate reader (Perkin Elmer) at the appropriate emission/excitation wavelengths, and the $IC_{50}$ (concentration inhibiting by 50% the enzyme activity) determined. The results are reported in Tables 1 and 2.

Example 21

Cytotoxicity Assay in Human Neuroblastoma Cell Line SH-SY-5Y

At time zero, the cells were seeded at $1.10^4/cm^2$ in 96 well plates in DMEM growth medium+10% heat inactivated FBS+2 mM l-Glutamine+100 U/mL-100 µg/mL Penicillin/Streptomycin.

After 72 hours at subconfluent phase of growth, the medium was removed and cells were incubated for 24 hours at 37° C. in 180 µl of neurobasal medium+2 mM l-Glutamine (Life Technologies) with or without test compounds (20 µl, at least 5 concentrations in triplicate).

At the end of incubation, 20 µl of Alamar Blue dye (AlamarBlue™ Assay Kit, Promega) were directly added to the cell medium.

Four hours after, the cytotoxicity was assessed by measuring the fluorescence at 530 nm excitation and 595 nm emission using Tecan Spectrafluor plate reader.

Before and at the end of the treatment, the cultures were monitored microscopically by an Olympus IX70 inverted light microscope matched to an Image Analyzer (Image Pro Plus, 5.1) to evaluate the cellular morphology.

Results are expressed in Table 1 as concentration inducing 50% of mortality.

Example 22

HERG Current in Transfected CHO Cell Lines

The inhibition of HERG current was tested in CHO cells stably expressing recombinant HERG channel.

To evaluate the effect of the test compounds on HERG currents, cells were clamped at −80 Mv, depolarised to 0 mV for 5 seconds allowing activation of HERG current and repolarised to −50 mV during 5 seconds allowing HERG tail current to deactivate. This procedure was repeated at a frequency of 0.06 Hz. The current amplitude upon repolarisation (HERG tail current) was measured before and after exposure to the test compound.

Inhibition of current was calculated as the difference between the amplitude of HERG tail current amplitude measured at the end of external bath perfusion period and HERG tail current measured at the end of test compound perfusion period (when steady-state effect is reached) divided by control HERG tail current.

Drug concentration-inhibition curves were obtained by plotting tonic blocks versus drug concentrations. Dose-response curves were fitted to the tonic block data, according to the logistic equation: $y=A2+(A1-A2)/[1+(x/IC_{50})^p]$. A1 and A2 are fixed values of 0 and 1 corresponding to 0 and 100% current inhibition, x is the drug concentration, $IC_{50}$ is the drug concentration resulting in 50% current inhibition and p is the corresponding slope factor.

The results are reported in Table 1.

Example 23

Maximal Electroshock Test (MES) in Mice

The maximal electroshock test (MES) is used commonly in the screening of anti-epileptic drugs in rodent models.

Animals and Apparatus: Male CD1 mice weighing 25 g were used. The procedure described by White et al. (White H. S., Woodhead J. H., Franklin M. R., Swinyard E. A., and Wolf H. H. Antiepileptic Drugs (1995) $4^{th}$ ed.: 99-110, Raven Press, Ltd., New York) was followed. An Ugo Basile electroconvulsive generator (Model ECT UNIT 7801) was used to deliver an electrical stimulus sufficient to produce a hindlimb tonic extensor response in at least 97% of control animals. The stimulus was delivered intra-aurally through clip electrodes in mice (0.7 seconds of a 40 mA shock, with a pulse train of 80 Hz having a pulse duration of 0.4 ms). The acute effect of compounds administered intraperitoneally or orally 15-60 minutes before MES induction were examined and compared with a vehicle control group. Ten mice were studied per group. Complete suppression of the hindlimb tonic extensor component of seizures was taken as evidence of anticonvulsant activity.

The compounds of the invention were administered orally or intraperitoneally at the doses of 3-30 mg/kg.

The results are expressed in Tables 3 and 4 as % of protection.

Example 24

Amphetamine Plus Chlordiazepoxide-Induced Hyperlocomotion in Mice

The anti mania activity, predictive of efficacy in bipolar disorders, was measured using the "Amphetamine plus chlordiazepoxide-induced hyperlocomotion in mice" model according to the following procedure.

In this model, mice are treated with a mixture of d-amphetamine plus an anxiolytic dose of the benzodiazepine, chlordiazepoxide (Rushton R and Steinberg H. Nature 1966; 211: 1312-3; R. Arban, et al. Behavioural Brain Research, 158: 123-132). The model has been claimed to mimic some aspects of mania in bipolar disorder. Importantly, the hyperactivity induced by the mixture of d-amphetamine and chlordiazepoxide could be prevented by prior administration of the established mood stabilizer, lithium, as well as other mood stabilizers drugs (e.g. magnesium valproate and carbamazepine). Therefore, this model has face and predictive validity as a model of bipolar disorders and represents a valuable tool to determine, if a test compound could be a potential mood stabilizer drug candidate.

D-amphetamine (Amph) (2.5 mg/kg ip) plus chlordiazepoxide hydrochloride (CDP) (3 mg/kg ip) were administered to male Albino Swiss mice (25-32 g) in a volume of 10 ml/kg. The locomotor activity was recorded using an automated Activity Cage LE 881 (Panlab) (45×45 cm). This system detects animal movements from 2 levels of 4 side infrared sensors placed all around the square cage. Mice were pretreated with the test compound (0.5-60 mg/kg po) and 30 min later, with Amph (2.5 mg/kg ip) or Amph jointly with CDP (3 mg/kg ip) and were placed individually in the motor activity cages. The locomotor activity was measured in terms of total distance travelled (cm) over a period of 30 min. Each group consisted of 8-10 mice.

Statistical analysis: a two-way analysis of variance (ANOVA) with Amph treatment factor and drug treatment factor was performed. Bonferroni's procedure was used for multiple comparison post hoc analysis.

D-amphetamine-chlordiazepoxide administration induced a significant increase in locomotor activity.

Orally administered a ralfinamide (Ralf), manufactured according to the process of this invention, was found active in this experimental model significantly decreasing the hyperactivity induced by Amph/CDP mixture (FIG. 1).

We claim:
1. High purity (S)-2-[4-(3-fluorobenzyloxy)benzylamino] propanamide (safinamide) or (S)-2-[4-(2-fluorobenzyloxy) benzylamino]propanamide (ralfinamide) of formula (Ia) or (Ib)

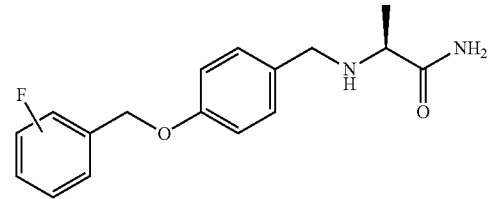

safinamide (Ia): 3-F
ralfinamide (Ib): 2-F and pharmaceutically acceptable acid salts thereof, produced by the process of:
submitting a Schiff base intermediate respectively of formula (VIa) or (VIb)

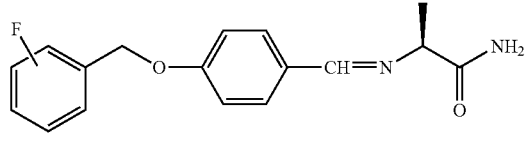

(VIa): 3-F
(VIb): 2-F to catalytic hydrogenation with hydrogen gas in the presence of a heterogeneous catalyst in a protic organic solvent and, when safinamide or ralfinamide are obtained in a free base form,
optionally converting said free base form to a salt thereof with a pharmaceutically acceptable acid.

2. The product as in claim 1 wherein the catalytic hydrogenation is carried out by using an heterogeneous catalyst selected from nickel, rhodium, platinum and palladium catalysts on an inert support in the presence of a solvent selected from lower aliphatic ($C_1$-$C_5$) alkanols.

3. The product as in claim 1 wherein the catalyst is a palladium or platinum catalyst.

4. The product as in claim 1 wherein the catalyst is wet 5% Pt/C (50% $H_2O$) or wet 10% Pd/C (50% $H_2O$).

5. The product as in claim 1 wherein the pharmaceutically acceptable acid is methanesulfonic acid.

6. The product as in claim 1 wherein the hydrogen pressure is between 1 and 10 bars and the temperature is between 10° C. and 70° C.

7. The product as in claim 6 wherein the hydrogen pressure is between 3 and 6 bars and the temperature is between 25° C. and 40° C.

8. The product as in claim 1 wherein the catalytic hydrogenation is carried out on a Schiff base intermediate (VIa) or (VIb) which has been prepared through iminoalkylation of 4-(3-fluorobenzyloxy)benzaldehyde (IVa) or 4-(2-fluorobenzyloxy)benzaldehyde (IVb)

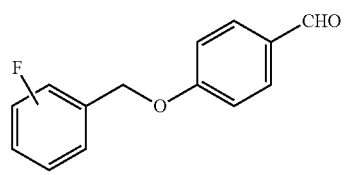

(IVa): 3-F
(IVb): 2-F with L-alaninamide in the presence of a protic organic solvent.

9. The product as in claim 8 wherein the L-alaninamide is employed as an acid addition salt thereof in the presence of a base in an amount sufficient to set free L-alaninamide from its salt.

10. The product as in claim 8 where the catalytic hydrogenation of the Schiff base intermediate is performed on the same reaction mixture resulting from the completion of the iminoalkylation reaction under conditions which provoke the precipitation of said Schiff base intermediate to obtain a suspension of said intermediate in the same reaction solvent.

11. The product as in claim 8 wherein the Schiff base intermediate resulting from the completion of the iminoalkylation reaction is isolated before undergoing the catalytic hydrogenation step.

12. The product as in claim 8 wherein the 4-(3-fluorobenzyloxy)benzaldehyde or 4-(2-fluorobenzyloxy)benzaldehyde of formula (IVa) or (IVb) employed as the starting material to obtain the Schiff base intermediate of formula (VIa) or (VIb) contains less than 0.03% (by weight), of the respective impurities 3-(3-fluorobenzyl)-4-(3-fluorobenzyloxy)benzaldehyde (Va) or 3-(2-fluorobenzyl)-4-(2-fluorobenzyloxy)benzaldehyde (Vb)

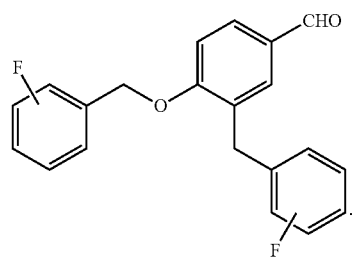

(Va): 3-F
(Vb): 2-F

13. The product according to claim 12 wherein the 4-(3-fluorobenzyloxy)benzaldehyde (IVa) or 4-(2-fluorobezyloxy)benzaldehyde (IVb) is obtained by alkylation of 4-hydroxybenzaldehyde with, respectively, a 3-fluorobenzyl or 2-fluorobenzyl derivative (IIIa) or (IIIb)

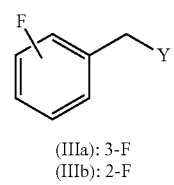

(IIIa): 3-F
(IIIb): 2-F where Y is a leaving group selected from Cl, Br, I, $OSO_2CH_3$ and $OSO_2$—$C_6H_4$-$pCH_3$, in the presence of a base, and is submitted to crystallization before the use in the successive reaction step.

14. The product as in claim 13 wherein Y is Cl.

15. The product as in claim 13 or 14 wherein the crystallization is carried out by adding an inert organic non-solvent to a solution of the 4-(3-fluorobenzyloxy)benzaldehyde (IVa) or 4-(2-fluorobenzyloxy)benzaldehyde (IVb) in an inert organic solvent.

16. The product as in claim 15 wherein the inert organic non-solvent is selected from lower aliphatic hydrocarbons and the inert organic solvent is selected from aromatic hydrocarbons.

17. The product as in claim 16 wherein the lower aliphatic hydrocarbon is n-hexane and the aromatic hydrocarbon is toluene.

18. The product as in any of claims 13 and 14 wherein the crystallization is carried out by dissolving the 4-(3-fluorobenzyloxy)benzaldehyde (IVa) or 4-(2-fluorobenzyloxy)benzaldehyde (IVb) in a hot solvent selected from cyclohexane, and a di(C3-C4)alkyl ether at reflux, and then cooling the solution to a temperature at or below room temperature.

19. The product as in any of claims 13 and 14 wherein the alkylation reaction is carried out under phase transfer conditions.

20. The product as in claim 19 wherein the alkylation under phase transfer condition is performed in a solid/liquid system wherein the reagents and the phase transfer catalyst are dissolved in a liquid organic phase and the solid phase is constituted by an inorganic base or a salt of 4-hydroxy benzaldehyde with said inorganic base.

21. The product as in claim 19 wherein the alkylation under phase transfer conditions is performed in a liquid/liquid system wherein the alkylating reagent 3-fluorobenzyl or 2-fluorobenzyl derivative of formula (IIIa) or (IIIb) is dissolved in a liquid organic phase and the 4-hydroxybenzaldehyde is dissolved in an aqueous phase as a salt with an inorganic base.

22. The product as in claim 19 wherein the phase transfer catalyst is selected from quaternary ammonium or phosphonium salts or polyethyleneglycols of low molecular weight.

23. The product of claim 22 wherein the amount of phase transfer catalyst employed is between 0.02 to 1 mole per mole of 4-hydroxybenzaldheyde.

24. The product as in claim 23 wherein the amount of phase-transfer catalyst is 0.1 to 1 mole per mole of 4-hydroxybenzaldehyde.

25. The product as in claim 20 wherein the organic solvent of the liquid organic phase is selected from dialkyl ethers and aromatic hydrocarbons.

26. The product as in claim 21 wherein the molar ratio between the alkylating reagent of formula (IIIa) or (IIIb), and 4-hydroxybenzaldehyde is between 0.6 and 1.5.

27. The product as in claim 20 wherein the temperature is between 60° C. and 160° C.

28. The product as in claim 20 wherein the inorganic base is selected from $Na_2CO_3$, $K_2CO_3$, NaOH and KOH, the temperature is between 80° C. and 120° C., and the ratio between the alkylating reagent of formula (IIIa) or (IIIb), and 4-hydroxybenzaldehyde is between 0.9 and 1.1.

29. The product as in claim 12 wherein safinamide or ralfinamide or their pharmaceutically acceptable acid salts, have a content of the respective impurity (S)-2-[3-(3-fluorobenzyl)-4-(3-fluorobenzyloxy)-benzylamino]propanamide (IIa) or (S)-2-[3-(2-fluorobenzyl)-4-(2-fluorobenzyloxy)-benzylamino]propanamide (IIIb)

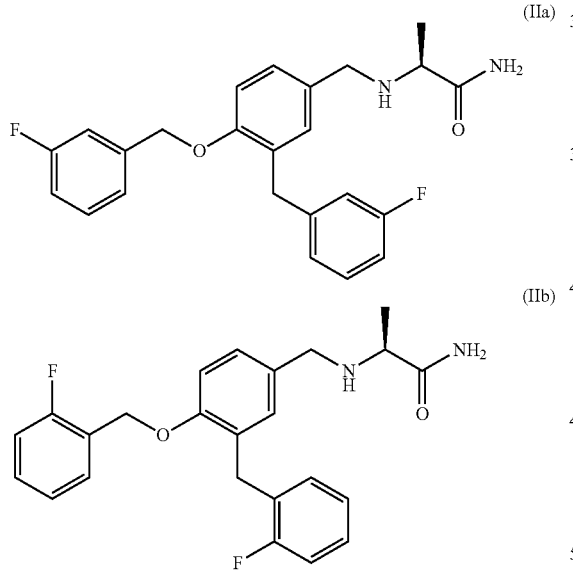

or their pharmaceutically acceptable acid salts, which is lower than 0.03% (by weight).

30. The product as in claim 29 wherein the pharmaceutically acceptable acid is methanesulfonic acid and the content of the respective impurity of formula (IIa) or (IIb) as the salt with methanesulfonic acid is lower than 0.01% (by weight).

31. The product as in claim 3 wherein the catalyst is platinum.

32. The product as in claim 4 wherein the catalyst is wet 5% Pt/C (50% $H_2O$).

33. The product as in claim 12 wherein the 4-(3-fluorobenzyloxy)benzaldehyde or 4-(2-fluorobenzyloxy)benzaldehyde of formula (IVa) or (IVb) employed as the starting material to obtain the Schiff base intermediate of formula (VIa) or (VIb) contains less than 0.01% (by weight), of the respective impurities 3-(3-fluorobenzyl)-4-(3-fluorobenzyloxy)benzaldehyde (Va) or 3-(2-fluorobenzyl)-4-(2-fluorobenzyloxy)benzaldehyde (Vb).

34. The product as in claim 18 wherein the hot solvent is diisopropylether.

35. The product as in claim 18 wherein the temperature is about 10-15° C.

36. A method for treating epilepsy comprising administering to a patient in need thereof an effective amount of high purity safinamide or a pharmaceutically acceptable acid salt thereof wherein the content of the impurity (S)-2-[3-(3-fluorobenzyl)-4-(3-fluorobenzyloxy)-benzylamino]propanamide of formula (IIa)

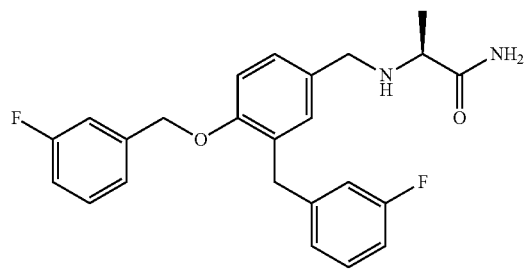

or a pharmaceutically acceptable acid salt thereof is lower than 0.03% (by weight).

37. A method for treating Parkinson's disease comprising administering to a patient in need thereof an effective amount of high purity safinamide or a pharmaceutically acceptable acid salt thereof wherein the content of the impurity (S)-2-[3-(3-fluorobenzyl)-4-(3-fluorobenzyloxy)-benzylamino]propanamide of formula (IIa)

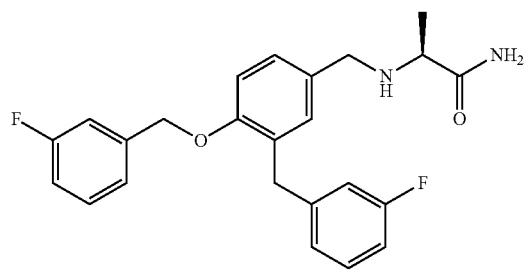

or a pharmaceutically acceptable acid salt thereof is lower than 0.03% (by weight).

38. A method for treating Alzheimer's disease comprising administering to a patient in need thereof an effective amount of high purity safinamide or a pharmaceutically acceptable acid salt thereof wherein the content of the impurity (S)-2-[3-(3-fluorobenzyl)-4-(3-fluorobenzyloxy)-benzylamino]propanamide of formula (IIa)

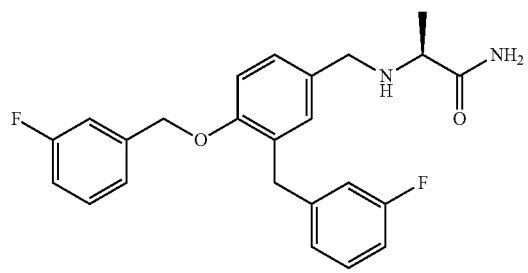

or a pharmaceutically acceptable acid salt thereof is lower than 0.03% (by weight).

39. A method for treating depression comprising administering to a patient in need thereof an effective amount of high purity safinamide or a pharmaceutically acceptable acid salt thereof wherein the content of the impurity (S)-2-[3-(3-fluorobenzyl)-4-(3-fluorobenzyloxy)-benzylamino]propanamide of formula (IIa)

(IIa)

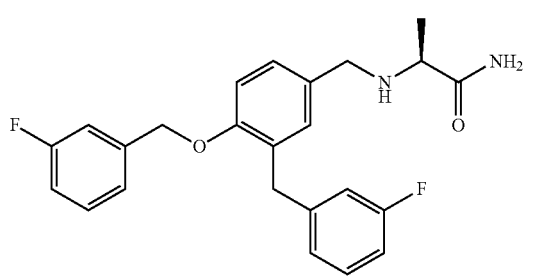

or a pharmaceutically acceptable acid salt thereof is lower than 0.03% (by weight).

40. A method for treating restless legs syndrome comprising administering to a patient in need thereof an effective amount of high purity safinamide or a pharmaceutically acceptable acid salt thereof wherein the content of the impurity (S)-2-[3-(3-fluorobenzyl)-4-(3-fluorobenzyloxy)-benzylamino]propanamide of formula (IIa)

(IIa)

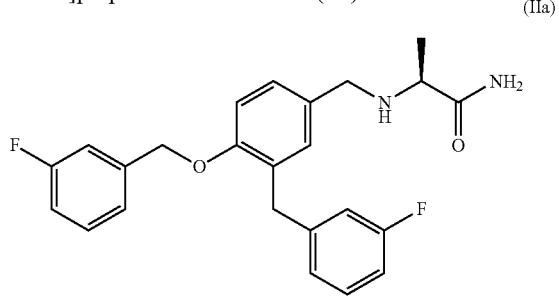

or a pharmaceutically acceptable acid salt thereof is lower than 0.03% (by weight).

41. A method for treating migraine comprising administering to a patient in need thereof an effective amount of high purity safinamide or a pharmaceutically acceptable acid salt thereof wherein the content of the impurity (S)-2-[3-(3-fluorobenzyl)-4-(3-fluorobenzyloxy)-benzylamino]propanamide of formula (IIa)

(IIa)

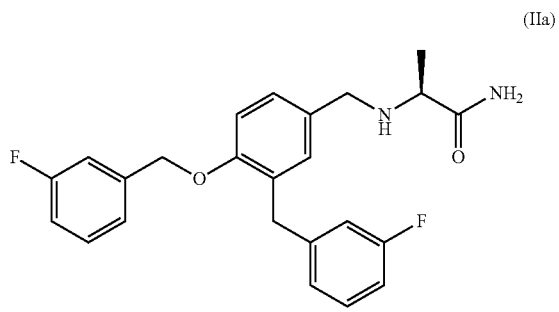

or a pharmaceutically acceptable acid salt thereof is lower than 0.03% (by weight).

42. A method for treating pain conditions comprising administering to a patient in need thereof an effective amount of high purity ralfinamide or a salt thereof with a pharmaceutically acceptable acid wherein the content of the impurity (S)-2-[3-(2-fluorobenzyl)-4-(2-fluorobenzyloxy)-benzylamino]propanamide of formula (IIb)

(IIb)

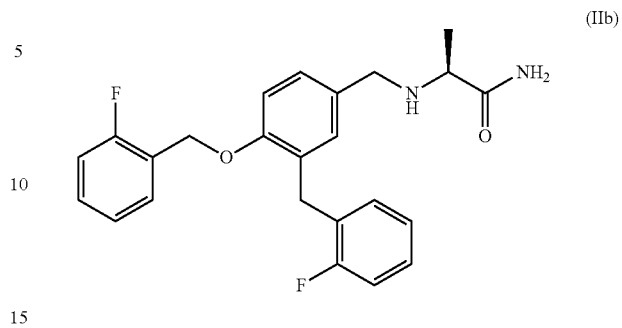

or a pharmaceutically acceptable acid salt thereof is lower than 0.03% (by weight).

43. A method for treating migraine comprising administering to a patient in need thereof an effective amount of high purity ralfinamide or a salt thereof with a pharmaceutically acceptable acid wherein the content of the impurity (S)-2-[3-(2-fluorobenzyl)-4-(2-fluorobenzyloxy)-benzylamino]propanamide of formula (IIb)

(IIb)

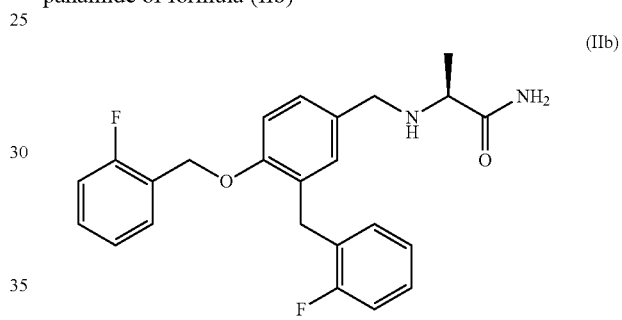

or a pharmaceutically acceptable acid salt thereof is lower than 0.03% (by weight).

44. A method for treating bipolar disorders comprising administering to a patient in need thereof an effective amount of high purity ralfinamide or a salt thereof with a pharmaceutically acceptable acid wherein the content of the impurity (S)-2-[3-(2-fluorobenzyl)-4-(2-fluorobenzyloxy)-benzylamino]propanamide of formula (IIb)

(IIb)

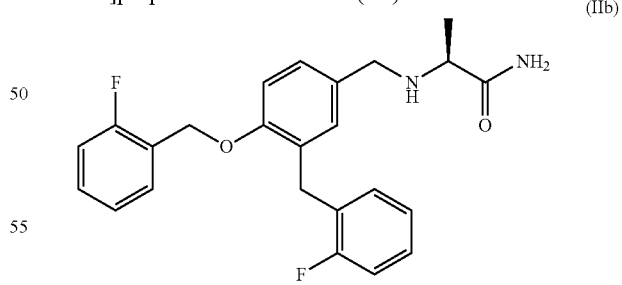

or a pharmaceutically acceptable acid salt thereof is lower than 0.03% (by weight).

45. A method for treating depressions comprising administering to a patient in need thereof an effective amount of high purity ralfinamide or a salt thereof with a pharmaceutically acceptable acid wherein the content of the impurity (S)-2-[3-(2-fluorobenzyl)-4-(2-fluorobenzyloxy)-benzylamino]propanamide of formula (IIb)

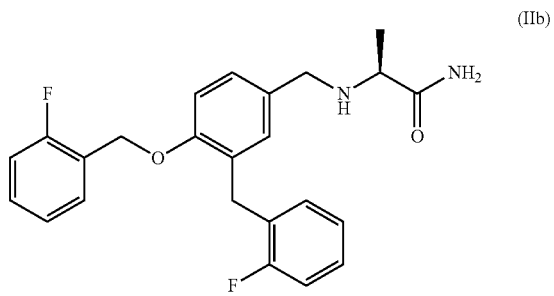

or a pharmaceutically acceptable acid salt thereof is lower than 0.03% (by weight).

46. A method for treating cardiovascular disorders comprising administering to a patient in need thereof an effective amount of high purity ralfinamide or a salt thereof with a pharmaceutically acceptable acid wherein the content of the impurity (S)-2-[3-(2-fluorobenzyl)-4-(2-fluorobenzyloxy)-benzylamino]propanamide of formula (IIb)

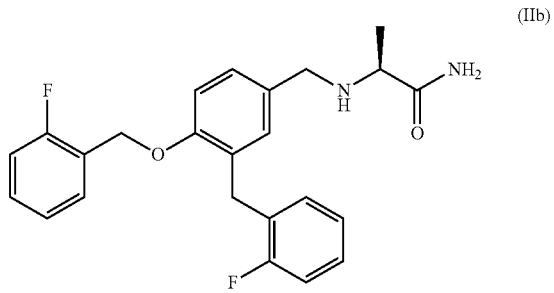

or a pharmaceutically acceptable acid salt thereof is lower than 0.03% (by weight).

47. A method for treating inflammatory disorders comprising administering to a patient in need thereof an effective amount of high purity ralfinamide or a salt thereof with a pharmaceutically acceptable acid wherein the content of the impurity (S)-2-[3-(2-fluorobenzyl)-4-(2-fluorobenzyloxy)-benzylamino]propanamide of formula (IIb)

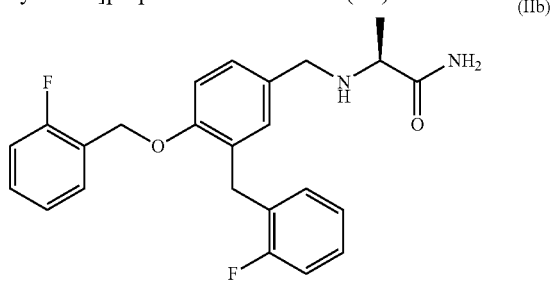

or a pharmaceutically acceptable acid salt thereof is lower than 0.03% (by weight).

48. A method for treating urogenital disorders comprising administering to a patient in need thereof an effective amount of high purity ralfinamide or a salt thereof with a pharmaceutically acceptable acid wherein the content of the impurity (S)-2-[3-(2-fluorobenzyl)-4-(2-fluorobenzyloxy)-benzylamino]propanamide of formula (IIb)

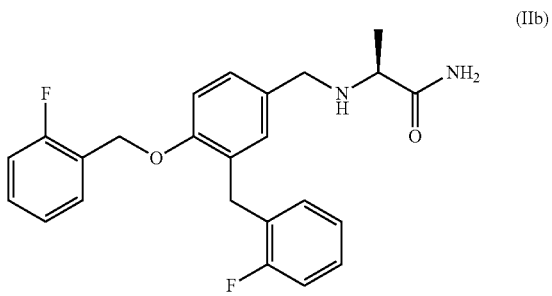

or a pharmaceutically acceptable acid salt thereof is lower than 0.03% (by weight).

49. A method for treating metabolic disorders comprising administering to a patient in need thereof an effective amount of high purity ralfinamide or a salt thereof with a pharmaceutically acceptable acid wherein the content of the impurity (S)-2-[3-(2-fluorobenzyl)-4-(2-fluorobenzyloxy)-benzylamino]propanamide of formula (IIb)

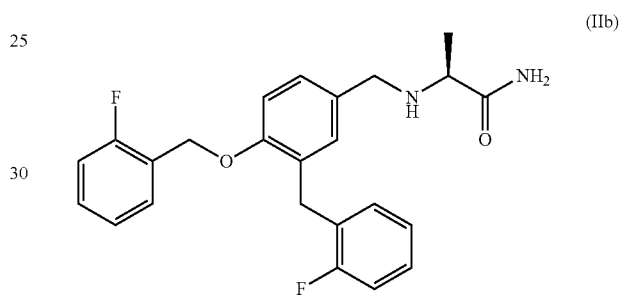

or a pharmaceutically acceptable acid salt thereof is lower than 0.03% (by weight).

50. A method for treating gastrointestinal disorders comprising administering to a patient in need thereof an effective amount of high purity ralfinamide or a salt thereof with a pharmaceutically acceptable acid wherein the content of the impurity (S)-2-[3-(2-fluorobenzyl)-4-(2-fluorobenzyloxy)-benzylamino]propanamide of formula (IIb)

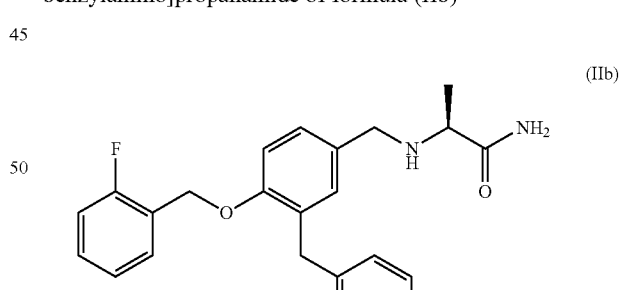

or a pharmaceutically acceptable acid salt thereof is lower than 0.03% (by weight).

* * * * *